(12) United States Patent
Usui et al.

(10) Patent No.: US 8,450,441 B2
(45) Date of Patent: May 28, 2013

(54) SYNTHETIC N-LINKED SIALO-GLYCAN-CONTAINING POLYMER AND METHOD FOR PRODUCING THE SAME

(75) Inventors: Taiichi Usui, Shizuoka (JP); Takeomi Murata, Shizuoka (JP); Takashi Suzuki, Shizuoka (JP); Ilpal Jwa, Shizuoka (JP); Yusuke Ohba, Choshi (JP); Tomoki Hamamoto, Choshi (JP); Toshitada Noguchi, Choshi (JP)

(73) Assignees: National University Corporation Shizuoka University, Shizuoka (JP); Shizuoka Prefectural Universities Corporation, Shizuoka (JP); Yamasa Corporation, Chiba (JP)

( * ) Notice: Subject to any disclaimer, the term of this patent is extended or adjusted under 35 U.S.C. 154(b) by 502 days.

(21) Appl. No.: 12/666,482
(22) PCT Filed: Jun. 24, 2008
(86) PCT No.: PCT/JP2008/061429
§ 371 (c)(1),
(2), (4) Date: Feb. 9, 2010
(87) PCT Pub. No.: WO2009/001805
PCT Pub. Date: Dec. 31, 2008

(65) Prior Publication Data
US 2010/0168366 A1 Jul. 1, 2010

(30) Foreign Application Priority Data
Jun. 28, 2007 (JP) .................................. 2007-170079

(51) Int. Cl.
*C08F 251/00* (2006.01)
*C07H 15/06* (2006.01)
*C12Q 1/70* (2006.01)

(52) U.S. Cl.
USPC ........... 527/312; 536/18.2; 536/18.7; 536/53; 536/55.1; 530/322

(58) Field of Classification Search
USPC ................... 435/5, 97; 527/312, 45; 530/322, 530/345, 395, 402, 401; 514/8; 536/55.1, 536/55.2
See application file for complete search history.

(56) References Cited

U.S. PATENT DOCUMENTS
5,079,353 A * 1/1992 Ratcliffe et al. ................. 536/53
2009/0269734 A1 10/2009 Suzuki et al.

FOREIGN PATENT DOCUMENTS
CA 2239296 * 4/1998
CA 2239296 A1 4/1998

(Continued)

OTHER PUBLICATIONS
Totani et al. Glycoprotein vol. 13 No. 5 pp. 315-326, 2003.*

(Continued)

*Primary Examiner* — James J Seidleck
*Assistant Examiner* — S. Camilla Pourbohloul
(74) *Attorney, Agent, or Firm* — Pearne & Gordon LLP

(57) ABSTRACT

A polymer containing an N-linked sialo-glycan wherein a sialo-glycan is condensed to a γ-polyglutamic acid using a chemical compound having an amino group on one end and a carboxyl group on another end and represented by the structural formula (I). Formula (I) (In the formula, Z means a hydroxy group or a residue represented by the formula (II), and n represents an integer of 10 or more, with the proviso that any one or more of the Z's is represented by the formula in (II).) Formula (II) (In the formula, X means a hydroxy group or an acetylamino group, $Y_1$ and $Y_2$ mean a hydroxyl group or an N-acetylneuraminic acid residue, L means a hydrocarbon, an m represents 0 or an integer of 1 or 2, with the proviso that $Y_1$ and $Y_2$ are not the same.)

1 Claim, 7 Drawing Sheets

FOREIGN PATENT DOCUMENTS

| | | |
|---|---|---|
| JP | 10-310610 A | 11/1998 |
| JP | 2002-514186 A | 5/2002 |
| JP | 2003-073397 A | 3/2003 |
| WO | 2007/026669 A1 | 3/2007 |

OTHER PUBLICATIONS

Totani et al; "Chemoenzymatic synthesis and application of glycopolymers containing multivalent sialyloligosaccharides with a poly(L-glutamic acid) backbone for inhibition of infection by influenza viruses", Glycobiology vol. 13, No. 5 pp. 315-326, 2003.

Ogata et al; "Chemoenzymatic synthesis of artificial glycopolypeptides containing multivalent sialyloligosaccharides with a y-polyglutamic acid backbone and their effect on inhibition of infection by influenza viruses", 2006.

International Search Report for PCT/JP2008/061429.

* cited by examiner

SYNTHETIC N-LINKED SIALO-GLYCAN-CONTAINING POLYMER AND METHOD FOR PRODUCING THE SAME

CROSS REFERENCE TO RELATED APPLICATIONS

This application is based upon and claims the benefit of priority from the prior Japanese Patent Applications No. 2007-170079, filed on Jun. 28, 2007, and PCT Application No. PCT/JP2008/061429, filed on Jun. 24, 2008, the entire contents of which are incorporated herein by reference.

BACKGROUND OF THE INVENTION

1. Field of the Invention

The present invention is related to a novel synthetic N-linked sialo-glycan-containing polymer having a polyglutamate backbone and an efficient method of producing the same.

2. Description of the Related Art

The influenza virus is one pathogen in which an effective treatment method or phylaxis method has not been discovered. Because the influenza virus has an extremely strong infectivity, antigen variation is repeated and a strain emerges with a different antigenicity until that point, there is a problem in that it is difficult to develop effective protection measures using a vaccine etc. Recently, there is growing concern with regards to the emergence of the human influenza virus which has its origins in the avian influenza virus. As a consequence, the development of an influenza virus absorbent or infection inhibitor for the prevention of the influenza virus is expected.

It is thought that infection of the influenza virus to a host cell is caused by hemagglutinin (HA) which is a surface protein of the virus recognizing and binding with sialic acid-containing glycoconjugates of the surface of the host cell as a receptor. It has been reported that the Influenza A virus which is isolated from Ayes preferentially binds with a glycan having NeuAc ($\alpha$2,3) Gal at a terminal, however, the human virus which is extremely similar to this virus shows a very high binding affinity for a NeuAc ($\alpha$2,6) Gal structure of the terminal.

In this way, because there are a variety of subtypes due to mutation in the influenza virus, a product is desired which has an anti-influenza effect which widely inhibits the binding of receptors regardless of the subtype of the virus as a more effective anti-influenza agent, and a sialic acid-containing glycan compound (sialo-glycan) is expected to be able to function as an infection inhibitor which inhibits binding to the virus receptor which is the first step of the influenza virus infection or as an influenza virus absorbent.

Conventionally, an attachment inhibition experiment of an influenza virus which uses hemagglutination inhibition activity as an index using various sialo-glycan compounds was performed. However, because the attachment inhibition activity of a virus is low or because the synthetic process is complex and impractical, an infection inhibitor of an influenza virus in which sialo-glycan is the active ingredient has still yet not been developed.

For example, a synthetic glycan polypeptide containing sialyl-N-acetyllactosamine with a molecular weight of 2,000-1,000,000 is disclosed in Japan Laid Open Patent 2003-73397 (patent document 1) and Glycobiology, 13, 315-326 (2003) (non-patent document 1), in which N-acetyllactosamine is introduced with a p-aminophenyl group as a linker to a side chain of the $\alpha$-polyglutamic acid as $\alpha$-polyglutamic acid backbone and further, a sialic acid is linked to the non-reducing terminal of the glycan, and it was confirmed as having an infection inhibition activity against a wide range of influenza virus isolated strains. This sialyl-N-acetyllactosamine binding synthetic glycan polypeptide is effective as an infection inhibitor or absorbent against the influenza virus, however, the raw material such as $\alpha$-polyglutamic acid, N-acetylglucosamine derivative (p-nitrophenyl glycoside) is an expensive chemical compound, and the manufacturing process is also cumbersome requiring extremely high manufacturing costs, whereas, infection inhibition activity $IC_{50}$ to the influenza virus 3-30 µg/ml is not a sufficient activity from a practical point of view.

In addition, a synthetic glycan polypeptide containing sialyl-N-acetyllactosamine in which the polypeptide part of the above stated synthetic glycan polypeptide containing sialyl-N-acetyllactosamine is converted into a $\gamma$-polyglutamic acid which can be obtained cheaply, or in which the linker part of the sialo-glycan part and the polyglutamic acid are converted into a cheap aminoalkylalcohol, is disclosed in International Laid Open Pamphlet, WO2007/02669 (patent document 2) and Bioorg. Med. Chem., 15, 1383-1393 (2007) (non-patent document 2), and it is reported that the obtained polymer has an inhibition activity of influenza virus infection tens of times greater compared to a conventional polymer.

BRIEF SUMMARY OF THE INVENTION

While the synthetic sialo-glycan containing polymer described in patent document 2 and non-patent document 2 can be synthesized from a cheap raw material, there are still many problems in actual production. First, a cellulase derived from *Trichoderma* which has been purified to a high level is required in the condensation between an asialo-glycan part and aminoalkylalcohol which becomes a linker, and because a reverse reaction of a hydrolase is used, there is a problem of an extremely low synthesis yield (about 1% of the glycan used) (problem 1).

In addition, in the synthesis of a synthetic sialo-glycan-containing polymer until now, aminoalkylalcohol coupled to an asialo-glycan part was used as a linker and condensation between an amino group of the linker and carboxyl group of a polyglutamic acid was performed using an excessive amount of reagent. In this way, a polyglutamic acid with a low solubility to an organic solvent is activated uniformly and it was possible to prevent disproportionation of a condensation reaction due to gelation etc. However, in the case where a sialo-glycan is used, a reaction occurs between a carboxyl group having sialic acid on a non-reducing terminal and an amino group of a linker end due to an excessive amount of reagent, and this method can not be applied for condensation between glycan parts to occur. Thus, synthesis was performed in a complex process wherein after coupling an asialo-glycan part and a linker and synthesizing an O-linked asialo-glycan, a polymer containing asialo-glycan was synthesized by condensing this O-linked asialo-glycan with a $\gamma$-polyglutamic acid, and finally sialic acid was transferred to a non-reducing terminal of the asialo-glycan using sialyltransferase derived from a rat (problem 2).

Furthermore, sialylating the asialo-glycan after condensing with the polyglutamic acid is more difficult than condensing with the polyglutamic acid after sialylating the asialo-glycan. For example, a sialyltransferase derived from microorganisms can not be used in a sialyltransferase reaction in the final process in a conventional method, and an animal (including human) derived sialyltransferase purified to a high degree is needed in order to prevent degradation of the polymer containing asialo-glycan, which in effect increased production costs and is not satisfactory as a practical method (problem 3).

As a result of repeated keen research which should solve the above described problem, the inventors of the present invention discovered that it is possible to easily make condensation of a glycan part and a linker highly efficient by amide bonding a chemical compound having an amino group on one end and a carboxyl group on the other end such as alkylcarboxylic acid introduced with an amino group as a linker to an amino sugar produced by chemically aminating 1 position, that is, by changing from an O-linked form of a glycan reducing terminal with a linker to an N-linked type.

In addition, it was also discovered that the novel N-linked sialo-glycan-containing polymer has an inhibition activity of influenza virus infection many times that of a conventional polymer with O-linked sialo-glycan-containing polymer.

Furthermore, it was also discovered that by using a hydrous mixed solvent different to convention in a condensation reaction of a sialo-glycan and polyglutamic acid, it is possible to improve the solubility of the polyglutamic acid and uniformly active esterify a carboxyl group in the polyglutamic acid even if an excessive amount of reagent is not used. Because an excess of reagent does not exist in a polyglutamic acid solution which has been active esterified in this way, it is possible to prevent a condensation reaction between sialo-glycans by an excessive amount of reagent during the addition of a sialo-glycan, and the present invention was completed by confirming that a condensation between a sialo-glycan part and polyglutamic acid via a linker could be performed highly efficiently without protecting the carboxyl group of the sialo-glycan.

Therefore, the present invention is represented by the structural formula (I) below, and is related to an N-linked sialo-glycan-containing polymer in which a sialo-glycan is linked to a γ-polyglutamic acid via a chemical compound having an amino group on one end and a carboxyl on the other end as a linker.

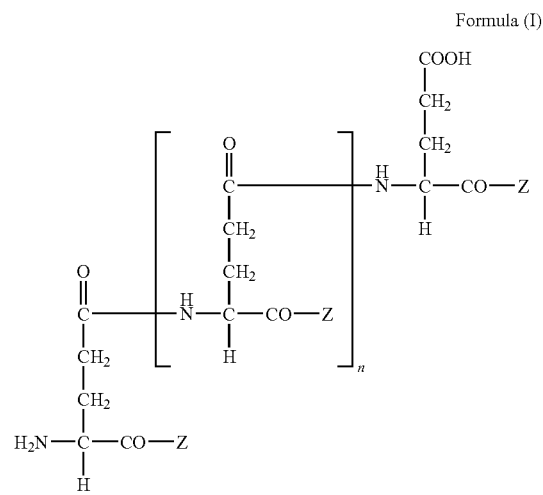

Formula (I)

(In the formula (I), Z means a hydroxy group or a residue represented by the formula (II), and n represents an integer of 10 or more, with the proviso that any one or more of the Z's is represented by the formula in (II).)

Formula (II)

(In the formula (II), X means a hydroxy group or an acetylamino group, $Y_1$ and $Y_2$ mean a hydroxyl group or an N-acetylneuraminic acid residue, L means a hydrocarbon, an m represents 0 or an integer of 1 or 2, with the proviso that $Y_1$ and $Y_2$ are not the same.)

In addition, the present invention is related to a production method (production method 1) of N-linked sialo-glycan-containing polymer comprised from the following process.

(Process 1)

A process for synthesizing an N-linked sugar primer by amidating 1 position of a reducing terminal of sugar and amide bonding a chemical compound having an amino group on one end and a carboxyl group on the other end as a linker.

(Process 2)

A process for synthesizing an N-linked asialo-glycan by extending a glycan using a glycosyltransferase to the sugar primer obtained in process 1 and synthesizing the asialo-glycan part to be synthesized to a non-reducing terminal according to necessity.

(Process 3)

A process for synthesizing a polymer containing asialo-glycan by condensing the N-linked asialo-glycan synthesized in process 2 to a carboxyl group side chain of a γ-polyglutamic acid.

(Process 4)

A process for obtaining by isolating sialo-glycan-containing polymer to be obtained by sialylating polymer containing asialo-glycan obtained in process 3 using a sialyltransferase.

Furthermore, the present invention is related to a production method (production method 2) of N-linked sialo-glycan-containing polymer comprised of the following processes.

(Process 1)

A process for synthesizing N-linked sugar primer by amidating 1 position of a reducing terminal of sugar and amide bonding a chemical compound having an amino group on one end and a carboxyl group on the other end as a linker.

(Process 2)

A process for synthesizing N-linked asialo-glycan by extending a glycan to the sugar primer obtained in process 1 using a glycosyltransferase according to necessity and synthesizing the sialo-glycan part to be synthesized to a non-reducing terminal of the sugar primer by sialylating with sialyltransferase.

(Process 3)

A process for activating a γ-polyglutamic acid using an active ester agent of a carboxyl group, condensing agent and/or additive and condensing the sialo-glycan synthesized in process 2 to a carboxyl group side chain of the polyglutamic acid.

A polymer containing sialo-glycan may be obtained by purifying and isolating in the next process the polymer containing sialo-glycan synthesized in process 3 of production method 2, and similarly a process may be arranged for purifying and isolating the polymer containing sialo-glycan produced by process 4 of production method 1.

Figure 1:
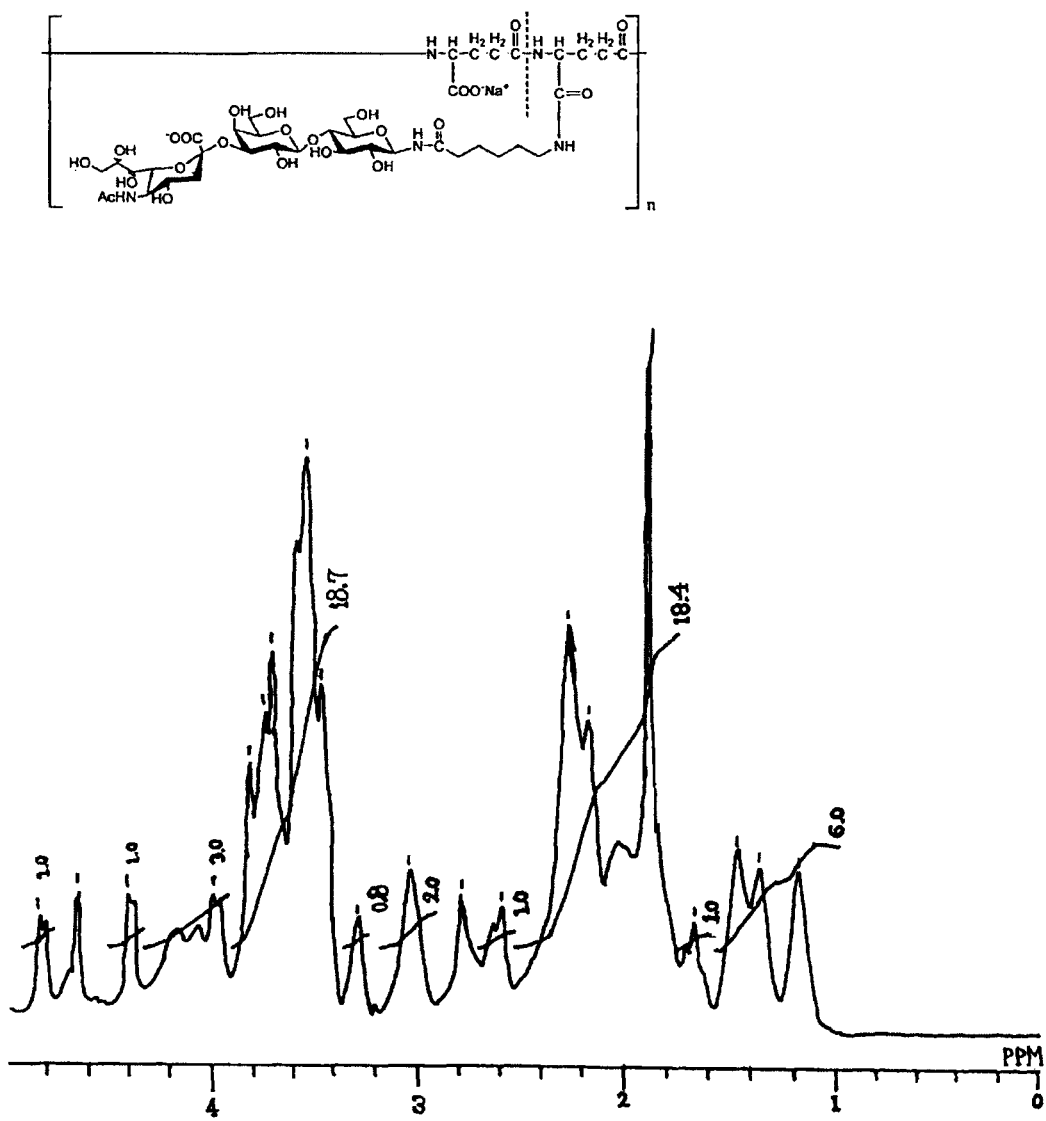
FIG. 1 shows the structure of Poly[Neu5Ac α2-3lactosylamine β-N-(ε-aminocaproyl)/γ-PGA] prepared in example 1 and a $^1$H-NMR spectrum.
Figure 2:
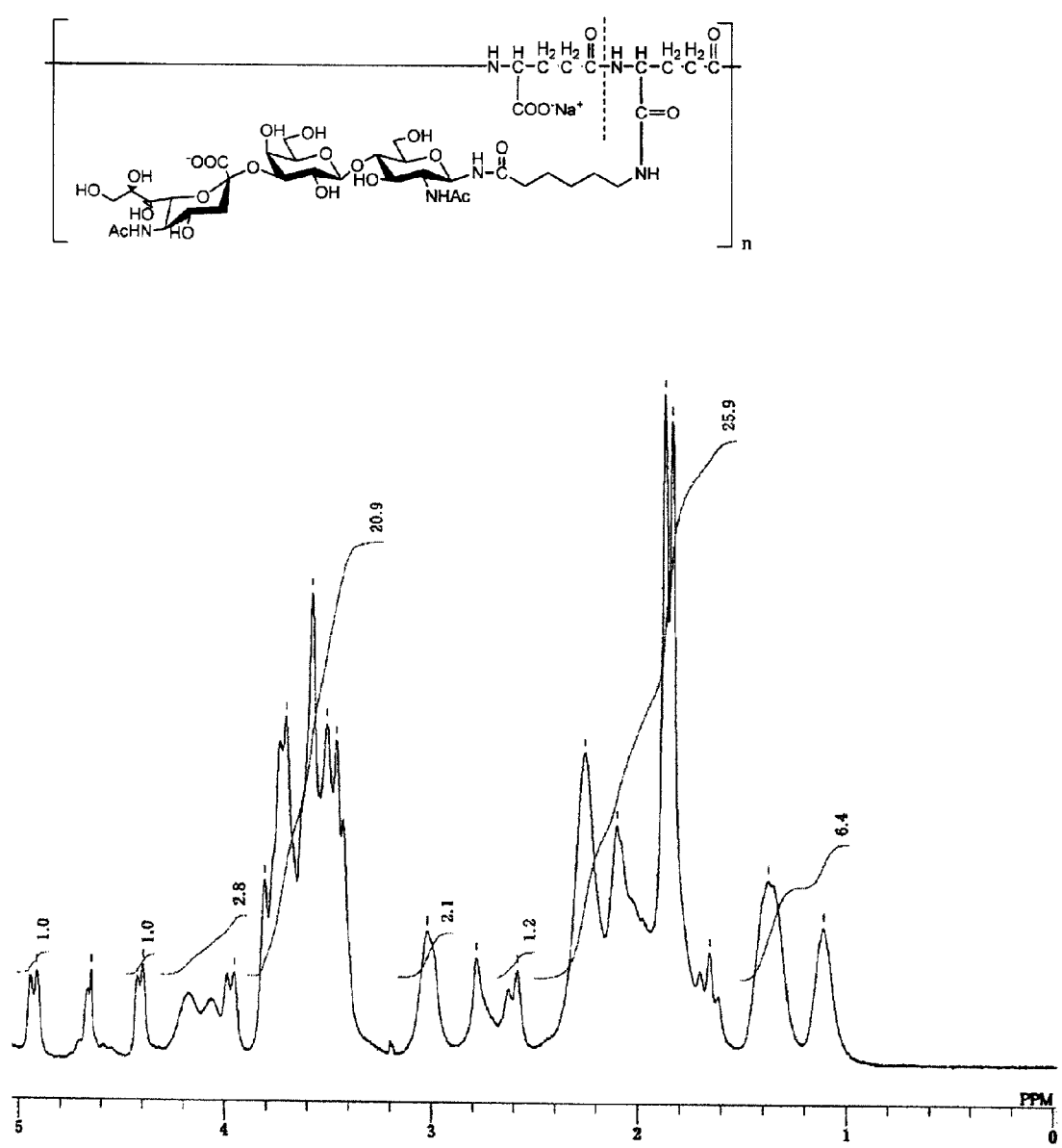
FIG. 2 shows the structure of Poly[Neu5Ac α2-3-N-acetyllactosaminylamine β-N-(ε-aminocaproyl)/γ-PGA] prepared in example 1 and a $^1$H-NMR spectrum.
Figure 3:
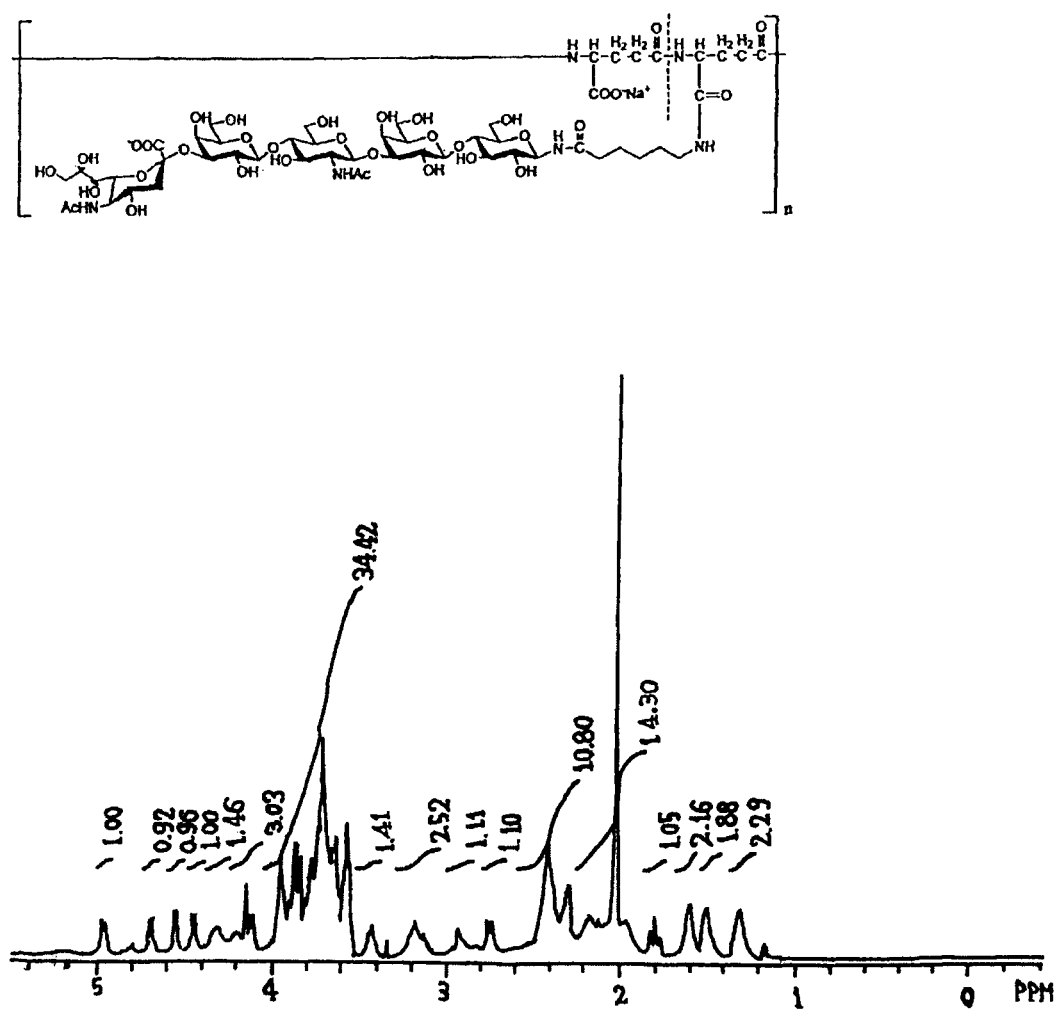
FIG. 3 shows the structure of Poly[Neu5Ac α2-3lacto-N-neotetraosylamine β-N-(ε-aminocaproyl)/γ-PGA] prepared in example 1 and a $^1$H-NMR spectrum.
Figure 4:
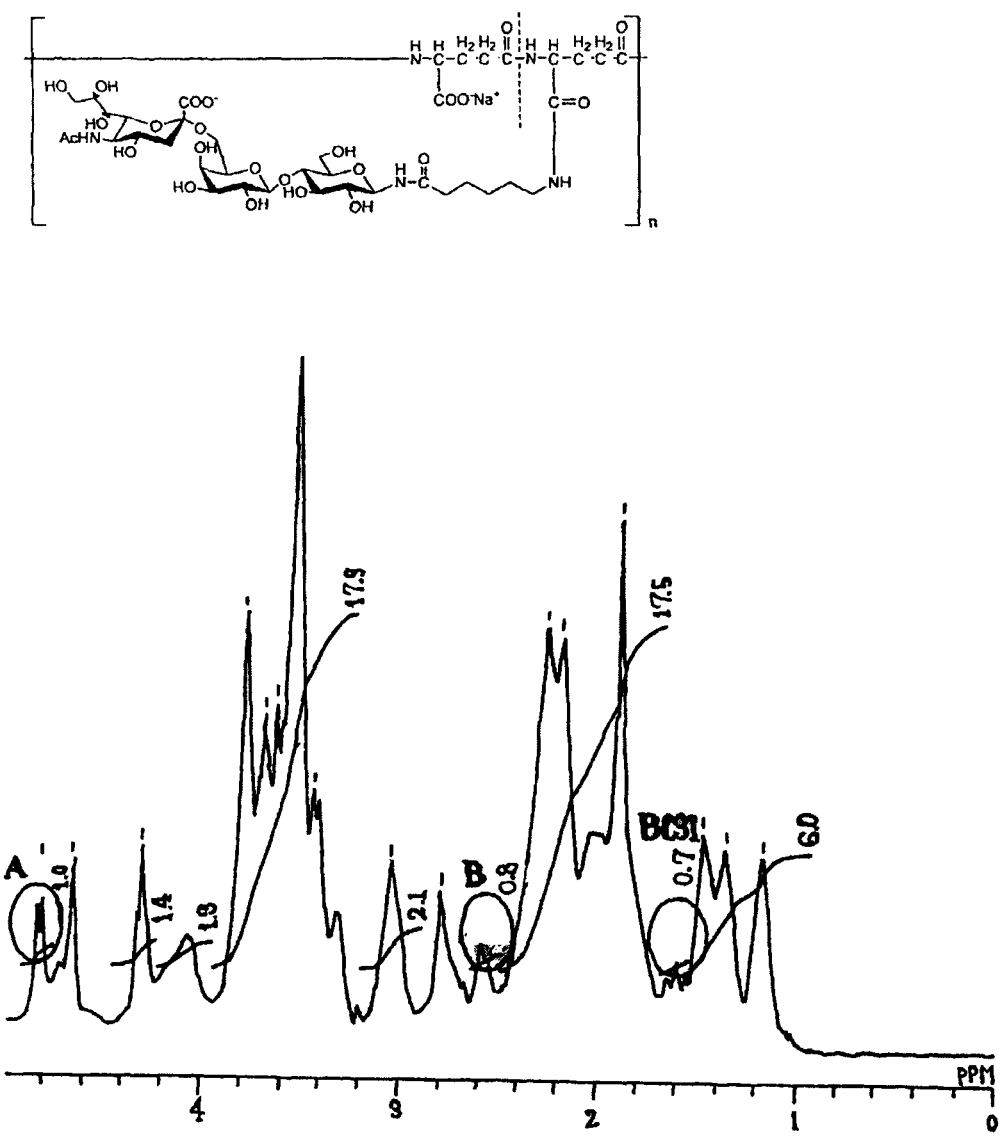
FIG. 4 the structure of Poly[Neu5Ac α2-6lactosylamine β-N-(ε-aminocaproyl)/γ-PGA] prepared in example 1 and a $^1$H-NMR spectrum.
Figure 5:
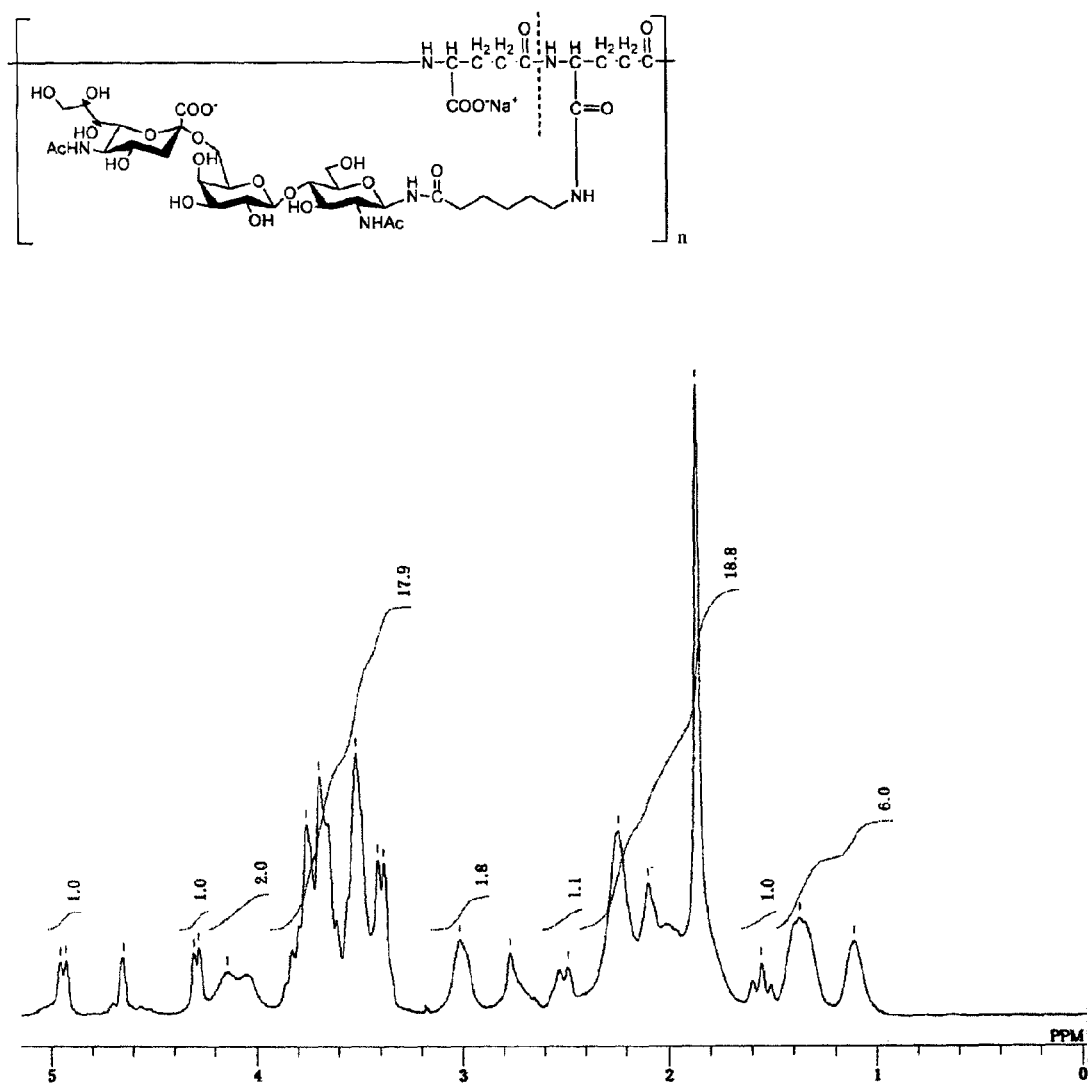
FIG. 5 shows the structure of Poly[Neu5Ac α2-6-N-acetyllactosaminylamine β-N-(ε-aminocaproyl)/γ-PGA] prepared in example 1 and a $^1$H-NMR spectrum.
Figure 6:
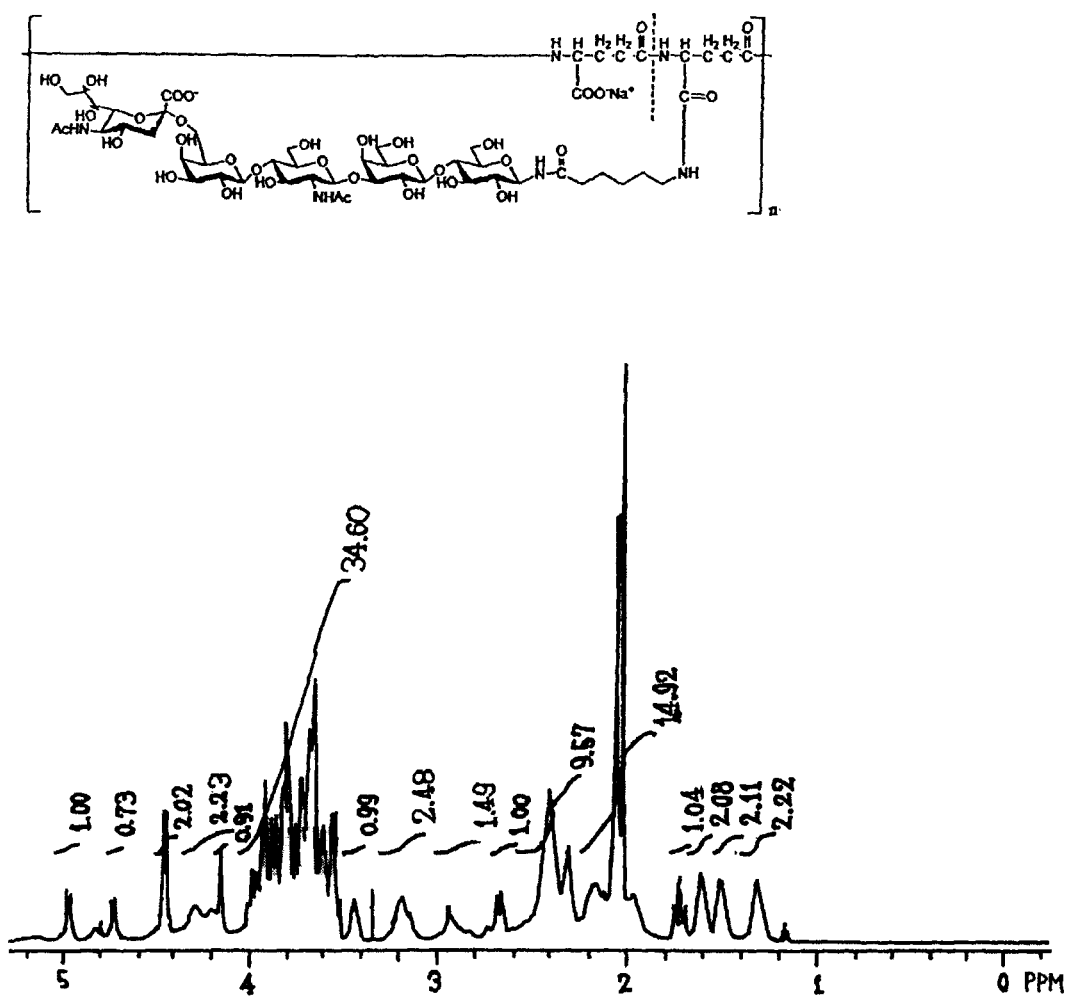
FIG. 6 shows the structure of Poly[Neu5Ac α2-6lacto-N-neotetraosylamine β-N-(ε-aminocaproyl)/γ-PGA] prepared in example 1 and a $^1$H-NMR spectrum.
Figure 7:
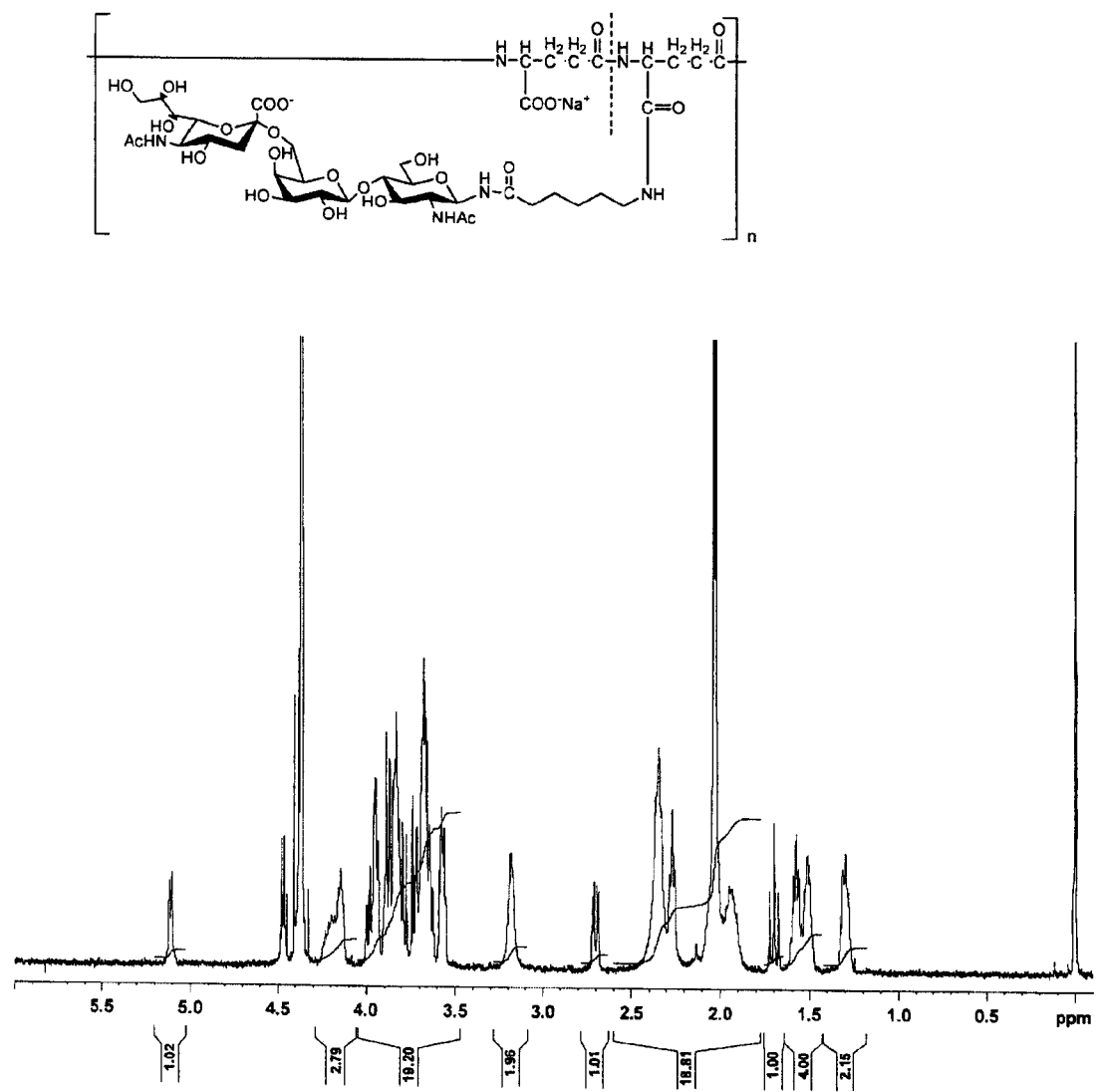
FIG. 7 shows the structure of Poly[Neu5Ac α2-6-N-acetyllactosaminsylamine β-N-(ε-aminocaproyl)/γ-PGA] prepared in example 2 and a $^1$H-NMR spectrum.

DETAILED DESCRIPTION OF THE INVENTION (1) N-linked Synthetic sialo-glycan-containing Polymer An N-linked synthetic sialo-glycan-containing polymer (also called N-linked synthetic sialo-glycan-containing polypeptide) of the present invention is shown by the structural formula (I) below.

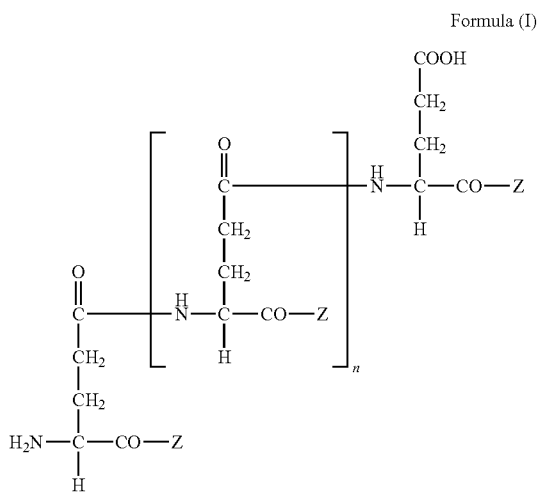

Formula (I)

(In the formula (I), Z means a hydroxy group or a residue represented by the formula (II), and n represents an integer of 10 or more, with the proviso that any one or more of the Z's is represented by the formula in (II).)

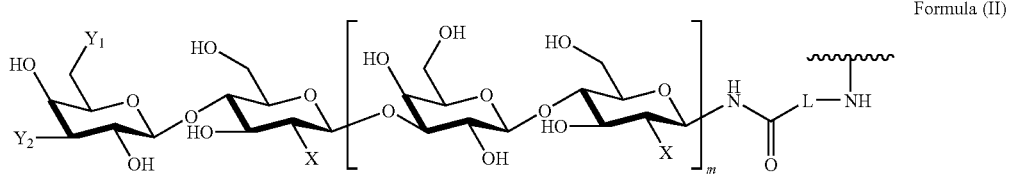

Formula (II)

(In the formula (II), X means a hydroxy group or an acetylamino group, $Y_1$ and $Y_2$ mean a hydroxyl group or an N-acetylneuraminic acid residue, L means a hydrocarbon, an m represents 0 or an integer of 1 or 2, with the proviso that $Y_1$ and $Y_2$ are not the same.)

In Formula (II), a hydrocarbon with a carbon number of 1-30 is preferred as the hydrocarbon represented by L, and may be a saturated hydrocarbon or an unsaturated hydrocarbon. Specifically, an alkyl group, an alkenyl group, an alkynyl group, cycloalkyl group, aryl group, aralkyl group, cycloalkyl substituted alkyl group, or a combination of any two or more of these condensed by an amide bond etc. can be exemplified.

Here, as an alkyl group, alkenyl group, alkynyl group, a straight chain or branched chain hydrocarbon having a carbon number of 1-20 can be exemplified. As a specific example, a straight chain alkyl group such as a methyl group, an ethyl group, an n-propyl group, an n-butyl group, an n-pentyl group, an n-hexyl group, an n-octyl group, an n-decyl, an n-dodecyl group, and an n-tetradecyl group, and a branch chain alkyl group such as an isopropyl group, an isobutyl group, a t-butyl group, and a 2-ethylhexyl group, can be exemplified.

As specific examples of an alkenyl group, a vinyl group, a propenyl group and an allyl group can be exemplified. As specific examples of an alkynyl group, an ethynyl group, a propynyl group and a butynyl group can be exemplified.

A cycloalkyl group having a carbon number of 3-10 and in particular a cycloalkyl group having a carbon number of 3-8, such as a cyclopropyl group, cyclopentyl group, and cyclohexyl group for example are preferred as a cycloalkyl group.

An aryl group having a carbon number of 6-14 such as a phenyl group, a tolyl group, and a naphthyl group are exemplified as an aryl group. An aralkyl group with a carbon number of 7-14, specifically a benzyl group and a phenethyl group are exemplified as an aralkyl group. A C3-C8 cycloalkyl substituted C1-C10 alkyl group, for example, a cyclopropylmethyl group, a cyclopentylmethyl group, a cyclohexylmethyl group, a cyclopropylethyl group, a cyclopentylethyl group, a cyclohexylethyl group, a cyclopropylpropyl group, a cyclopentylpropyl group, and a cyclohexylpropyl group are exemplified as a cycloalkyl substituted alkyl group.

In addition, this hydrocarbon may include a substituted group such as a hydroxyl group, an azide group, a cyano group, an alkoxyl group, a cycloalkyloxy group, an aryloxy group, and a carboxyl group which may be esterified. Furthermore, two or more of these compounds may be used by condensation by an amide bond and combined.

An N-acetylneuramic acid residue represented by Y1 or Y2 is represented by formula (III) below, and a hydroxyl group, carboxyl group or acetylamino group may be chemically modified the same or differently by a halogen group, alkyl group or acyl group.

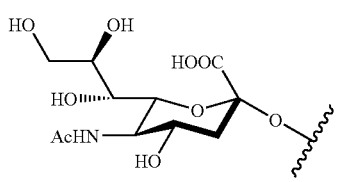

Formula (III)

This type of N-linked sialo-glycan-containing polymer may be one of either a salt or a free acid and as a salt, for example, an alkali metal salt (for example, sodium salt, potassium salt), an alkaline-earth metal salt (for example, calcium salt, magnesium salt), an organic base salt (for example, trimethylamine salt, triethylamine salt, pyridine salt, picoline salt, dicyclohexylamine salt) are exemplified. In addition, the N-linked sialo-glycan-containing polymer may be a hydrate or solvate with alcohol etc.

In addition, the molecular weight of the N-linked sialoglycan-containing polymer has a range of for example 2000-5,000,000, a glutamine acid unit degree of polymerization (n) is in a range of 10-10,000, and an introduction rate of sialoglycan with respect to a glutamine acid residue is in a range of 10-80%.

(2) Production Method of the N-linked sialo-glycan-containing Polymer
(Production Method 1)
(Process 1) Synthesis of a Sugar Primer Process 1 is for obtaining an N-linked sugar primer by amide bonding a chemical compound having an amino group and a carboxyl group on each end respectively as a linker to a 1-amino sugar in which a 1 position hydroxyl group of a reducing terminal of an easily obtainable sugar has been chemically aminated.

As a sugar used in a reaction, if a hydroxyl group in an anomeric position has activity in a subsequent amination, other hydroxyl groups may be modified or substituted such as a monosaccharide, a disaccharide or a glycan. Specifically, glucose, N-acetylglucosamine, lactose, N-acetyllactosamine may be exemplified.

1-amino sugar may be prepared by a known method, for example, after saturating an ammonium hydrogen carbonate in the sugar solution described above (water, methanol, ethanol, or a mixed solvent of these), reacting at 10-70° C., more preferably 30-50° C. for 1-100 hours while stirring depending on necessity (Biochem. Biophy. Acta, 1226, 117-122 (1997)), or inserting the above described sugar solution into a pressure resistant container and reacting at 10-70° C. or more preferably 30-50° C. for 1-100 hours in a state where an ammonium gas has been saturated while stirring depending on necessity (J. Org. Chem., 23, 1309-1319 (1958)).

In the case where an ammonium hydrogen carbonate is used in the synthesis of 1-amino sugar, purification is performed by removing the excess reagent by crystallization or removing the reagent by repeating azeotropy with water, and in the case where ammonia gas is used, isolation and purification are performed by filtrating a reaction liquid and washing the retrieved crystal using an organic solvent (ethanol, diethyl ether etc.) for use in the next reaction.

As a chemical compound having an amino group and a carboxyl group which are linkers, a compound represented by NH$_2$-L-COOH where L is a hydrocarbon as explained above. Specifically, it is possible to exemplify a ω-amino acid such as an alkylcarboxylic acid introduced with an amino group. The amino group in the compound having an amino group and a carboxyl group may also be protected by a usual method by a protective group. As the protective group used here, it is preferred that a protective group which is stable under the subsequent reaction conditions and which can deprotect under conditions which do not influence a sialo-glycan structure, for example, a trifluoroacetyl group, a benzyl group, a benzyloxycarbonyl group, a 9-fluorenylmethyloxycarbonyl group etc. are exemplified.

A condensation reaction which forms an amide bond between a 1-amino sugar and a linker with a protected amino group can be performed by processing in an organic solvent (dimethylformamide, dimethylsulfoxide etc.) under the existence of a base (triethylamine, tributylamine etc.) with a condensation agent (carbonyldiimidazole, chlorcarbonic acid ethyl, tetramethyl-O-(1H-benzotriazole-1-yl) uronium hexafluorophosphate etc.).

The required amount of a base and a condensation agent may be the equivalent or more to a linker usually. In addition, a general acylation reaction catalyst such as 4-N,N-dimethylaminopyridine etc. may be added depending on necessity.

The condensation reaction can be performed from −10° C. to 100° C. and is particularly preferred to be performed from 0° C. to 30° C. In this way, by using a 1-amino sugar and a linker in a condensation reaction, N-linked sugar primer in which the linker is linked to a 1 position part which has been aminated on a reducing terminal is synthesized.

The synthesized N-linked sugar primer can be isolated and purified using a separation and purification means of a glycan usually, for example, the synthesized N-linked sugar primer can be isolated and purified by appropriately combining reverse phase ODS column chromatography and ion exchange chromatography.

[Process 2] Synthesis of asialo-glycan Part

In process 2, glycosyltransferase (β1,4-galactosyltransferase, β1,3-N-acetylglucosaminyltransferase etc.) is added to a reaction system containing the sugar primer (N-linked sugar primer) synthesized in process 1 and a sugar donor (sugar-nucleotide:uridine 5'-diphosphogalactose, uridine 5'-diphosphoacetylglucosamine etc.), the glycan is extended to the non-reducing terminal side of the N-linked sugar primer and an asialo-glycan part is synthesized on the non-reducing terminal side of the N-linked sugar primer.

As a glycosyltransferase added to the reaction system any form may be used as long as it has the desired enzyme activity. In order to improve the ease of preparing an enzyme as well as preparation efficiency, the enzyme is preferably obtained by using an enzyme preparation technology called recombinant DNA technology in which the enzyme gene is cloned and highly expressed within the cell of a microorganism to prepare a large amount of the enzymes.

As an enzyme sample, specifically it is possible to exemplify an enzyme preparation obtained from microbial cells, treated cells or the like. It is possible to prepare the microbial cells by a method in which microorganisms are cultivated by a common method with a medium in which they can grow and are gathered by centrifugal separation or the like. Specifically, when explained using a bacterium which belongs to *Escherichia coli* as an example it is possible to use a bouillon medium, an LB medium (1% tryptone, 0.5% yeast extract, 1% common salt) or 2.times.YT medium (1.6% tryptone, 1% yeast extract, 0.5% common salt). After inoculating a seed cell into the medium, it is cultivated while stirring according to necessity for about 10 to 50 hours at a temperature between 30 and 50 degrees C., the cultivated solution which is obtained is separated by centrifugation, and by gathering the microorganism cells it is possible to prepare microbial cells having a desired enzyme activity.

As treated cells of a microorganism, it is possible to exemplify destroyed cells or altered cell walls or cell membranes obtained by treating the cells according to a general treatment method. As a general treatment method of cells, mechanical destruction (by using for example, a Waring blender, French press, homogenizer, mortar, and the like), freezing and thawing, autolysis, drying (by for example, lyophilization, air drying, and the like), enzyme treatment (by using lysozyme and the like), ultrasonic treatment, and chemical treatment (by for example, acid, alkaline treatment, and the like), can be used.

As an enzyme preparation, a crude enzyme or a purified enzyme obtained from the above stated treated cells can be exemplified. The crude enzyme or the purified enzyme can be obtained by performing a common enzyme refining means (for example, salting-out treatment, isoelectric focusing sedimentation treatment, organic solvent sedimentation treatment, dialysis treatment and various chromatography treatments, and the like) on a fraction having the enzyme activity obtained from the above stated treated cells.

Each commercially available product can be used for a sugar nucleotide as the sugar donor. The concentration used can be appropriately set from a range of 1-200 mM or more preferably 5-50 mM.

A glycosyltransferase is added to a reaction system containing the above described sugar primer and sugar nucleotide so that each becomes 0.001 units/ml or more and more preferably 0.01-10 units/ml, and synthesis of an asialo-glycan part is performed by reacting while stirring according to necessity for 1-100 hours at 5-50° C. or more preferably 10-40° C. In this way, a linker having an amino group and a carboxyl group on a reducing terminal is linked, and an N-linked asialo-glycan having an asialo glycan part on a non-reducing terminal is obtained.

The N-linked asialo-glycan prepared in this way may be isolated using a glycan usual separation purification means, for example, it is possible to perform isolation and purification by appropriately combining reverse phase ODS column chromatography and ion exchange chromatography etc.

Furthermore, the glycan extension reaction of process 2 may be performed if necessary and the glycan extension reaction may be omitted depending on the type of sugar used in process 1. For example, in the case of linking a 1-amino sugar with an aminated sugar polymer having 2 or more sugars to a linker compound in process 1, because the N-linked sugar polymer which is obtained has an asialo-glycan part on a non-reducing terminal and a linker on a reducing terminal, it is possible to omit process 2 and use the reaction product of process 1 as the N-linked asialo-glycan as it is in process 3 described next.

[Process 3] Condensation of asialo-glycan and γ-polyglutamic acid

Process 3 is a process in which the N-linked asialo-glycan synthesized in process 2 is chemically condensed to the carboxyl group side chain of γ-polyglutamic acid via the amino group of the linker on the reducing terminal.

In process 3, the N-linked asialo-glycan synthesized in process 2 has an asialo-glycan part on a non-reducing terminal and a chemical compound derived amino group introduced as a linker on a reducing terminal. In the case where the amino group within the linker is protected by a protection group, the protection group of the amino group within the linker is deprotected by a usual method before performing the condensation reaction of process 3, and in some cases, using the N-linked asialo-glycan in a condensation reaction with γ-polyglutamic acid after isolation and purification using a usual glycan purification means (gel filtration, reverse phase ODS column chromatography and ion exchange chromatography etc.).

A commercially available product can be used as the γ-polyglutamic acid used as a raw material polymer.

It is possible to perform a condensation reaction according to a known method (patent documents 1 and 2, non-patent documents 1 and 2). By this type of condensation reaction, a condensation reaction product (N-linked asialo-glycan-containing polymer) in which the N-linked asialo-glycan is condensed to the carboxyl group of the γ-polyglutamic acid is obtained.

[Process 4]

In process 4, the N-linked asialo-glycan-containing polymer synthesized in process 3 is sialylated using a sialyltransferase and the desired N-linked sialo-glycan-containing polymer is obtained in isolation. The process in which N-linked asialo-glycan-containing polymer is sialylated using a sialyltransferase can be performed by a known method (patent documents 1 and 2, non-patent documents 1 and 2). Isolation and purification of the synthesized N-linked sialo-glycan-containing polymer may be performed by a usual method used in the protein purification, for example, isolation and purification can be performed by appropriately combining dialysis or gel filtration etc.

The introduction rate of the sialo-sugar in the N-linked sialo-glycan-containing polymer prepared in this way can be measured by $^1$H-NMR spectrum. For example, a value in which an integrated value of characteristic peak in a chemical compound used in a sialo-glycan or linker is divided by an integrated value of characteristic peak in a polyglutamic acid may be used as the sugar introduction rate.

(3) Production Method of an N-linked sialo-glycan-containing Polymer (Production Method 2)

[Process 1] Synthesis of a Sugar Primer

Process 1 is for obtaining an N-linked sugar primer by forming an amide bond between a chemical compound having an amino group and a carboxyl group as a linker and a 1 position hydroxyl group of an easily available sugar which has been chemically aminated. This is the same as production method 1.

[Process 2] Synthesis of a sialo-glycan Part

In process 2, glycosyltransferase (β1,4-galactosyltransferase, (β1,3-N-acetylglucosaminyltransferase, α2,6-sialyltransferase etc.) which fits the purpose is added to a reaction system containing a sugar primer and a sugar donor (sugar-nucleotide:uridine 5'-diphospho galactose, uridine 5'-diphospho-N-acetylglucosamine, cytidine 5'-monophospho-N-acetylneuramic acid etc.), and the sialo-glycan part is synthesized.

It is possible to perform preparation and reaction of an enzyme under the same preparation and reaction conditions as process 2 of production method 1. Furthermore, the above described process 2 is described as a process which includes a stage for performing an extension reaction of a glycan and a stage for performing a sialylation reaction. That is, here process 2 is described as a process for performing a sialylation reaction using a sialyltransferase (α2,3-sialyltransferase, α2,6-sialyltransferase etc.) after performing an extension reaction of a glycan using the sugar primer, sugar donor and glycosyltransferase (β1,4-galactosyltransferase, β1,3-N-acetylglucosaminyltransferase) used in production method 1.

However, in production method 2, the extension reaction of the glycan in process 2 may be performed or omitted according to necessity. That is, process 2 in production method 2 is a process for synthesizing the sialo-glycan part and not the asialo-glycan part on the non-reducing terminal of the N-linked sugar primer, and the extension reaction can be omitted according to the sugar primer synthesized in process 1. For example, in the case where a sugar polymer having two or more sugars on the non-reducing terminal is aminated and linked with a linker as a 1-amino sugar in process 1, the extension reaction of the glycan is not performed in process 2, and the reaction product (N-linked asialo-glycan) of process 1 is sialylated and an N-linked sialo-glycan may be synthesized.

By this process, a linker having an amino group on a reducing terminal is linked and an N-linked sialo-glycan in which a sialo-glycan part is synthesized on the non-reducing terminal is obtained. The N-linked sialo-glycan prepared in this way may be isolated using a usual separation and purification means of a glycan, for example, by appropriately combining reverse phase ODS column chromatography and ion exchange chromatography.

[Process 3] Condensation of sialo-glycan and γ-polyglutamic acid

Process 3 is a process in which the N-linked sialo-glycan synthesized in process 2 is chemically condensed to the carboxyl group side chain of γ-polyglutamic acid via the amino group of the linker on the reducing terminal.

The N-linked sialo-glycan synthesized in process 2 has a sialo-glycan part on a non-reducing terminal and a chemical compound derived amino group introduced as a linker on a reducing terminal. In the case where the amino group within the linker is protected by a protection group in process 3, the protection group is deprotected by a usual method and in some cases, the N-linked asialo-glycan is used in a condensation reaction with γ-polyglutamic acid after isolation and purification using a usual glycan purification means (gel filtration, reverse phase ODS column chromatography and ion exchange chromatography etc.).

A commercially available product can be used for the γ-polyglutamic acid used as a raw material polymer.

A mixed solvent of water and a buffer solution (a carbonate etc. with the pH preferred to be from 4 to 10) and an organic solvent (dimethylformamide or dimethylsulfoxide etc.) can be used as a solvent used in the condensation process. At this time, it is possible to use a solvent with a percentage of contained water from 1% to 80% and more preferably 10% to 50%.

After activating a γ-polyglutamic acid using an active esterified agent of a carboxyl group, a condensation agent and/or an additive under the existence of a base (triethylamine or tributylamine) within the above described solvent and a condensation reaction can be performed by reacting with the N-linked sialo-glycan from which the protective group of a linker is removed by the above described deprotection reaction.

p-Nitrophenyl chloroformate, disuccinylcarbonate, carbonyldiimidazole etc. are exemplified as an active esterification agent of a carboxyl group, dicyclohexylcarbodiimide, diisopropylcarbodiimide, N-ethyl-N'-3-diimethylaminopropyl-carbodiimide (and those hydrochloride salts), benzotriazole-1-yl-tris(dimethylamino)phosphonium hexafluorophosphate etc. are exemplified as a condensation agent, and N-hydroxysuccinimide, 1-hydroxybenzotriazole, 3-hydroxy-4-oxo-3,4-dihydro1,2,3-benzotriazole etc. can be exemplified as an additive.

A combination of an active esterification agent, condensation agent and or additive can be appropriately selected according to the sialo-glycan-containing polymer to be synthesized, preferably a combination of a condensation agent and an additive can be exemplified, and more specifically a combination of N-ethyl-N'-3-diimethylaminopropylcarbodiimide and N-hydroxysuccinimide are suitable.

The required amount of the N-linked sialo-glycan from which a protected group of an amino group is deprotected may be added according to the sugar substitution percentage of the desired sialo-glycan-containing polymer, and usually, may be the equivalent of 0.1 or more with respect to a unit of the glutamic acid in γ-polyglutamic acid. In addition, the required amount of the active esterification agent, condensation agent and additive may be about the same as the required amount of sialo-glycan. Furthermore, the required amount of a base used in a condensation reaction may be the equivalent of 1 or more with respect to a unit of the glutamic acid in γ-polyglutamic acid.

The condensation reaction can be performed from −10° C. to 100° C. In addition, a catalyst for a general acylation reaction such as 4-N-N-dimethylaminopyridine may be added according to necessity.

Furthermore, by dissolving γ-polyglutamic acid in a solvent containing water it is possible to turn a carboxyl group of the γ-polyglutamic acid into an easily reaction state. As a result, in the case where γ-polyglutamic acid is dissolved in a solvent containing water, it is possible to reduce the amount of an added reagent (condensation agent) required for condensation reaction with sialo-glycan. Specifically, while equivalent of 3 or more by weight of a condensation agent with respect to a sialo-glycan was required in a conventional method, according to the present invention which uses a solvent containing water, the condensation agent may be the same amount as the sialo-glycan.

Furthermore, using a condensation agent having an equivalent amount or lower than a unit of the glutamic acid in γ-polyglutamic acid and an additive which can form a stable active ester within the solvent containing water to convert the γ-polyglutamic acid into an active ester it is possible to practically and completely consume the condensation agent which is the cause of a side reaction of the sialo-glycan, and it is possible to turn the carboxyl group of the γ-polyglutamic acid into an easy reaction state within the solvent containing water. Consequently, it is possible to reduce a side reaction of the carboxyl group, and avoid the bad effects stated above due to the use of an excess of a reagent when condensing a sialo-glycan-containing polymer and γ-polyglutamic acid. As a result, according to the production method 2, it is possible to condense the sialo-glycan-containing polymer with γ-polyglutamic acid, and sialylation is not necessary after the asialo-glycan has been condensed with polyglutamic acid as in the production method 1.

[Process 4]

In process 4, the N-linked sialo-glycan-containing polymer synthesized in process 3 is isolated and purified, and a desired sialo-glycan-containing polymer is obtained. Isolation and purification of the synthesized sialo-glycan-containing polymer may be performed by a usual method used in the protein purification, for example, isolation and purification can be performed by appropriately combining dialysis or gel filtration etc.

The introduction rate of the sialo-sugar in the N-linked sialo-glycan-containing polymer prepared in this way can be measured by $^1$H-NMR spectrum. For example, a value in which an integration value of characteristic peak in a chemical compound used in a sialo-glycan or linker is divided by an integration value of characteristic peak in a polyglutamic acid may be used as the sugar introduction rate.

(4) Usability of a sialo-glycan-containing Polymer

Because N-linked synthetic sialo-glycan-containing polymer of the present invention has an inhibition activity of influenza virus infection many times greater than a conventional O-linked sialo-glycan-containing polymer in addition to ease of synthesis, it can be applied to various means for preventing influenza virus infection and the spread of influenza. For example, use of a virus absorbent in the filter of a mask, air cleaner, or air conditioner can be exemplified. Furthermore, according to the differences in specificity of receptor recognition of the human influenza virus and avian influenza virus (difference of sialic acid binding manner of sialo-glycan of the receptor), using α2,3 linked sialo-glycan-containing polymer and α2,6 linked sialo-glycan-containing polymer as a base material, it is possible to analyze the receptor recognition specificity of the influenza virus and therefore it is also possible to be applied to surveillance of a novel influenza virus.

Furthermore, the present invention can be applied to various viruses not particularly limited to an influenza virus corresponding to the sialo-glycan-containing polymer which is used. For example, paramyxovirus family, parainfluenza virus family, rotavirus, adenovirus, coronavirus and polyomavirus are exemplified. Highly pathogenic avian influenza A virus, human influenza A virus and human influenza B virus can be exemplified as the influenza virus.

EXAMPLES

Next, examples of the present invention will be explained. Furthermore, the present invention is not limited by the examples described below.

[Material Preparation Method and Analysis Method]

(1) HPLC

All the samples were analyzed after filtration of 0.45 μm filter. The following were used as the analysis conditions.

Column: Mightysil Si60 (φ4.6×250 mm)

Column temperature: 40° C.

Flow speed: 1.0 ml/min

Detection wavelength: 210 nm

Solvent: 90% $CH_3CN$

Or
Column: YMC Pro C18RS (φ6.0×150 mm)
Column temperature: 30° C.
Flow speed: 1.0 ml/min
Detection wavelength: 210 nm
Solvent: 20% $CH_3CN$-20 mM $KH_2PO_4$
(2) NMR
Analytical instrument: JEOL EX-270 NMR spectrometer, JEOL lamda 500FT NMR spectrometer
Bruker AV-500 NMR spectrometer
External Standard: TPS [sodium3-(trimethylsilyl)-propionate]
Solvent: $D_2O$
Temperature: 25° C. or 60° C.
Sample Tube: φ3 or 5 mm
(3) Enzyme Preparation
3-1. Preparation of β1,4-galactosetransferase (β1,4-GalT)
It was performed according to the description in WO2007/026669.
3-2. Preparation of Human β1,3-N-acetylglucosaminyltransferase (β3GnTII)
It was performed according to the description in document (Protein Expr. Purif., 35, 54-61 (2004)).
3-3. sialyltransferase
(3-3-1) rat sialyltransferase
α2,3-sialyltransferase (Rat, Recombinant, *Spodoptera, frugiperda*), α2,6-sialyltransferase (Rat, Recombinant, *Spodoptera, frugiperda*) were purchased from Calbiochem Ltd.
(3-3-2) Preparation of α2,3-Sialyltransferase (α2,3-SiaT)
It was performed according to the example in the description in WO2007/026669.
(3-3-3) Preparation of α2,6-Sialyltransferase (α2,6-SiaT)
It was performed according to the example in the description in WO2007/026669.
(4) Materials (Reaction Substrate and Reagent)
Lactose Monohydrate, 5-amino-1-pentanol was purchased from Wako Pure Chemical Industries, Ltd. γ-PGA was purchased from Meiji Seika Co, Ltd. Sugar nucleotide (UDP-GlcNAc, UDP-Gal, CMP-NeuAc) was purchased from Yamasa Corporation. LacNAc was purchased from Yaizu Suisankagaku Industry Co, Ltd. Trifluoroacetic Anhydride, $MnCl_2.4H_2O$ was purchased from Wako Pure Chemical Industries, Ltd. α-PGA, BOP, HOBt and BSA were purchased from Sigma-Aldrich Co.
The abbreviations of the materials used are as follows.
pNP: p-Nitrophenol
pAP: p-Aminophenol
Lac: Lactose (Gal (β1-4) Glc)
Gal: Galactose
LacNAc: N-Acetyllactosamine (Gal (β1-4) GlcNAc)
NeuAc: N-Acetylneuraminic acid
GlcNAc: N-Acetylglucosamine
α-PGA: α-Polyglutamic acids
γ-PGA: γ-Polyglutamic acid
DMSO: Dimethyl sulfoxide
DMF: Dimethyl formamide
DIEA: N,N-Diisopropylethylamine
UDP-GlcNAc.2Na: Uridine 5'-diphospho N-acetylglucosamine, disodium salt
UDP-Gal.2Na: Uridine 5'-diphospho-α-D.-galactose disodium salt
HBTU: o-(Benzotriazol-1-yl) tetramethyluronium hexafluorophosphate
HOSu: N-Hydroxysuccinimide
EDC: 1-Ethyl-3-(3-dimethylaminopropyl) carbodiimide hydrochloride
BOP: Benzotriazol-1-yloxytris-(dimethylamino)phosphonium hexafluorophosphate
HOBt: 1-Hydroxybenzotriazole hydrate
PBS: 10 mM Phosphate buffered saline (pH 7.4)
TPS: Sodium 3-(trimethylsilyl)-propionate
CMP NeuAc: Cytidine-monophospho-N-acetylneuraminic acid Example 1

Synthesis of Each Type of Synthetic sialo-glycan-containing Polymer by Production Method 1

First, a process (1-A) for synthesizing a chemical compound (6-Trifluoroacetamidohexanoic acid) having an amino group and carboxyl group on an end, a process (1-B) for synthesizing a 1-amino sugar and a process (1-C) for synthesizing an N-linked sugar primer by condensing the linker chemical compound synthesized in process 1-A with the 1-amino sugar synthesized in process 1-B, will be explained.

(1-A) Synthesis of 6-Trifluoroacetamidohexanoic acid

Pyridine (70 ml) was added to Methyl 6-aminohexanoate hydrochloride (10 g, 55 mmol) and dissolved. This was ice-cooled and stirred and a reaction was begun by adding while dropping Trifluoroacetic acid anhydride (25 ml, 180 mmol). Every 5 minutes from the start of the reaction, the reaction was confirmed using phosphomolybdic acid color reaction by thin layer chromatography (TLC: development solution chloroform: acetone=9:1). After 2 hours, after confirming that the raw material has been consumed by TLC, about the same amount of crushed ice as the reaction solution was added and the reaction was stopped, 280 ml of a saturated sodium bicarbonate water solution was added and the reaction solution was neutralized. After concentrating the reaction solution an appropriate amount of acetone was added and concentration was performed again. This process was repeated about 3 times. Then, after dissolving the reaction solution with $H_2O$, the solution was transferred to a separating funnel dispensed by an equal amount of chloroform and $H_2O$, and a large amount of saturated sodium bicarbonate which exists was removed by collecting a chloroform fraction. Next, this chloroform fraction was concentrated and applied to a silica gel column chromatography (3.5×50 cm) equilibrated (10 ml/min) with chloroform:acetone=9:1. Sampling of a moving layer which passed through a column every 20 ml was performed. By TLC (development solution chloroform:acetone=9:1), the product of the elution fraction was confirmed using a phosphomolybdic acid color reaction. The desired product was confirmed in a fraction number of 25-56 (500-1120 ml). This was concentrated and Methyl 6-Trifluoroacetamidohexanate which was the desired product of this process was obtained with a weight of 12.4 g and yield of 93%.

Next, after dissolving Methyl 6-trifluoroacetamidohexanoate (3.7 g, 15.4 mmol) in 10 mM of a borate buffer pH8.0 (3000 ml), a porcine liver derived carboxylesterase (2160U, 1.2 ml) was added, and a reaction performed at 30° C. After 72 hours had passed since the start of the reaction, after boiling for 10 minutes at 100° C. and stopping the reaction, the reaction solution was concentrated and applied to a silica gel column chromatography (2.0×30 cm) equilibrated (10 ml/min) with chloroform:acetone=8:2. After fractionating into 20 ml per tube, the product was confirmed using a phosphomolybdic acid color reaction using TLC (development solution chloroform:acetone=8:2). After concentrating a fraction which is No. 5-15 (100-300 ml) including the desired product, the product was freeze dried and 6-Trifluoroacetamidohexanoic acid was obtained (weight: 3.1 g yield: 89%).

(1-B) Chemical Synthesis of 1-amino Sugar

A sugar was dissolved in a methanol solution (MeOH) and a 1-amino sugar was prepared by either saturating an ammonia gas or dissolving ammonium hydrogen carbonate. Lactose, N-acetyllactosamine (LacNAc), or N-acetylglucosamine was used as the sugar.

(1-B-1) Chemical Synthesis of β-Lactosylamine

Lactose (5.0 g, 0.014 mol) was put into a pressure resistant glass container and dissolved by 95% MeOH containing 0.5% $CH_3COOH$ (117 ml). Then, after ice-cooling the reaction solution, the reaction solution was ammonia saturated using ammonia gas. After ammonia saturation, the lid of the pressure resistant glass container was shut tight and a reaction was performed at 40° C. while stirring. After 48 hours has passed since the start of the reaction, ethanol (110 ml) was added and the reaction was stopped. Next, the reaction solution was filtrated using a glass filter, washed in sequence using ethanol (500 ml) and diethyl ether (500 ml) and β-Lactosylamine was obtained with a weight of 4.5 g and yield of 95% as a white powder.

(1-B-2) Chemical Synthesis of 3-N-Acetyllactosaminylamine

LacNAc (1.0 g, 2.6 mmol) and ammonium bicarbonate (0.21 g, 2.6 mmol) was put into a pressure resistant glass container and dissolved by MeOH (8 ml). Then, after ice-cooling the reaction solution, the reaction solution was ammonia saturated using ammonia gas. After ammonia saturation, the lid of the pressure resistant glass container was shut tight and a reaction was performed at 40° C. while stirring. After 120 hours has passed since the start of the reaction, ethanol (8 ml) was added and the reaction was stopped. Next, the reaction solution was filtrated using a glass filter, washed in sequence using ethanol (50 ml) and diethyl ether (50 ml) and β-N-Acetyllactosaminylamine was obtained with a weight of 0.71 g and yield of 71% as a white powder.

(1-B-3) Chemical Synthesis of β-N-Acetylglucoaminylamine

N-Acetylglucosamine (5.0 g, 22.6 mmol) and ammonium hydrogen carbonate (40 g) was dissolved in distilled water (50 ml) and stirred at 40° C. Progress of the reaction was confirmed by TLC (development solution AcOEt:MeOH:AcOH:$H_2O$=4:3:3:2, coloring with anisaldehyde, Rf:S.M.=0.65, Prod.=0.48). After confirming that the raw material had been consumed by TLC, the reaction solution was cooled and an excess amount of ammonium hydrogen carbonate was deposited and removed by filtrating. Concentration was performed under reduced pressure until the filtration was about 10 ml, and after cooling the ammonium hydrogen carbonate was removed by again performing filtration of the deposited ammonium hydrogen carbonate. Distilled water was added to the filtration, and by repeating the process of concentration under reduced pressure about 3 times, any remaining ammonium hydrogen carbonate was removed and a substance having an aspect such as wheat gluten was obtained. This was dissolved in a small amount of distilled water and by freeze drying, 7.4 g of 8-N-Acetylglucoaminylamine was obtained as a white powder.

[1-C] Chemical and Enzymatic Synthesis of Each Type N-linked Sugar Primer

[1-C-1] Chemical Synthesis of N-(ε-Trifluororoacetamidocaproyl)-β-lactosylamine

After dissolving 6-Trifluororoacetamidohexanoic acid (334 mg, 1.47 mmol) in an organic solvent (DMSO: 2.6 ml), a base (DIEA: 1.3 ml, 7.35 mmol) and a condensation agent (HBTU: 557 mg, 1.47 mmol) was added and stirred for 5 minutes. Following this, β-Lactosylamine (500 mg, 1.47 mmol) which was dissolved in DMSO (5.3 ml) in a different container in advance was added and a reaction was performed at room temperature while stirring. The time course of the reaction was analyzed by TLC (chloroform:methanol:water=7:3:0.5) using an orcinol sulfate color reaction. The reaction was stopped after 5 hours since the start of the reaction and applied to a silica gel column chromatography (3.5×60 cm) equilibrated (10 ml/min) with chloroform:methanol:water=7:3:0.5. After fractionating into 30 ml per tube, the product was confirmed using an orcinol sulfate color reaction by TLC (development solution chloroform:methanol:water=7:3:0.5). After concentrating a fraction which is number 68-135 (2040-4050 ml) including the desired product, the product was freeze dried and N-(ε-Trifluororoacetamidocaproyl)-β-lactosylamine was obtained as an N-linked sugar primer with a weight of 685 mg and yield of 82%.

[1-C-2] Chemical Synthesis of N-(ε-Trifluororoacetamidocaproyl)-β-N-acetyllactosaminylamine After dissolving 6-Trifluororoacetamidohexanoic acid (41 mg, 0.18 mmol) in DMSO (330 μl), DIEA (160 μl, 0.9 mmol) and HBTU (68 mg, 0.18 mmol) was added and stirred for 5 minutes. Following this, β-N-acetyllactosaminylamine (70 mg, 0.18 mmol) which was dissolved in DMSO (660 μl) in a different container in advance was added and a reaction was performed at room temperature while stirring. The time course of the reaction was analyzed by TLC (chloroform:methanol:water=7:3:0.5) using an orcinol sulfate color reaction. The reaction was stopped after 5 hours since the start of the reaction and applied to a silica gel column chromatography (3.5×60 cm) equilibrated (10 ml/min) with chloroform:

methanol:water=7:3:0.5. After fractionating into 30 ml per tube, the product was confirmed using an orcinol sulfate color reaction by TLC (development solution chloroform:methanol:water=7:3:0.5). After concentrating a fraction which is number 65-90 (1950-2700 ml) including the desired product, the product was freeze dried and N-(ε-Trifluororoacetamidocaproyl)-β-N-acetyllactosaminylamine was obtained as an N-linked sugar primer with a weight of 81 mkg and yield of 75%.

Next, in the process 1-C-3, β-N-Acetylglucoaminylamine (GlcNAc-NH$_2$) which is a 1-amino sugar synthesized in 1-B-3 described above is condensed with a linker chemical compound with a protected amino group and an N-linked sialo-glycan is obtained is explained below in detail.

[1-C-3] Chemical Synthsis of N-(ε-Trifluororoacetamidocaproyl)-β-N-acetylglucoaminylamine MeOH (5 ml) was added to 6-Aminohexanoic acid (0.538 g, 4.1 mmol), Triethylamine (0.86 ml, 6.2 mmol) and suspended. To this, Ethyl trifluoroacetate (0.75 ml, 6.2 mmol) was dropped and stirred at room temperature (about 22° C.) for 1 hour. After confirming that the raw material was consumed by TLC (development solution AcOEt:MeOH:AcOH:H$_2$O=4:3:3:2, ninhydrin color reaction, Rf:S.M.=0.66, Prod.=none), the reaction solution was concentrated under reduced pressure. DMF was added to a residue and concentration under reduced pressure was repeated 3 times, with any remaining reagent etc. removed. The residue was dissolved in DMF (40 ml) and after cooling at 0° C. in an ice bath, Ethyl chlorocarbonate (0.78 ml, 8.2 mmol) and triethylamine (1.14 ml, 8.2 mmol) was added. After stirring for 10 minutes at 0° C., this was added to a DMF (40 ml) suspended solution of GlcNAc-NH$_2$ (3.1 g, 8.2 mmol calculated at purity of 75%), taken out from the ice bath and stirred for 1 hour while gradually returning the temperature to room temperature. The reaction solution was again cooled in an ice bath, added with distilled water (10 ml) and after stopping the reaction, the deposited hydrochloride salt was removed by filtration. The filtrate was concentrated under a reduced pressure and by an azeotropic operation using distilled water, any remaining DMF was removed. The residue was prepared to 40 ml in distilled water and applied to ODS column (CV=200 ml) equilibrated with 5% acetonitrile. After fractionating at a flow rate of 400 ml/hr, 1Fr=20 ml, the product was confirmed by TLC and HPLC, and the elute fraction was collected. After concentrating an eluting fraction under reduced pressure, the residue was dissolved in a small amount of distilled water and freeze dried, N-(ε-Trifluororoacetamidocaproyl)-β-N-acetylglucosaminylamine (GlcNAc-6AHA-TFA), an N-linked asialo-glycan which has an amino group protected by a protective group was obtained as a desired product with a weight of 0.63 g and yield of 36%.

Next, the N-linked sugar primer synthesized in process 1-C-1 described above used as a sugar receptor, reacted with a sugar donor under the existence of a glycosyltransferase and the glycan is extended to a non-reducing terminal is explained in process 2 below.

(2) Enzymatic Synthesis of N-(ε-Trifluororoacetamidocaproyl)-β-lacto-N-neotetraosylamine 50 mg (0.09 mmol) of N-(ε-Trifluororoacetamidocaproyl)-β-Lactosylamine which becomes a receptor, 117 mg (0.18 mmol) of a sugar nucleotide (UDP-GlcNAc.2Na) as a donor, and 14.5 mg (0.07 mmol) of MnCl$_2$.4H$_2$O was dissolved in 150 mM Tris-HCl buffer (pH6.8, 5,7 ml), and after adding 0.09 ml of 1% (w/v) NaN$_3$ as a preservative, 3.3 ml (250 mU) of a purified glycosyltransferase (β3GnTII) was added and reacted at 37° C. After 144 hours, when transfer of GlcNAc of the donor substrate had progressed 100%, the reaction was stopped by boiling the reaction solution for 5 minutes. Next, 111 mg (0.18 mmol) of a different sugar nucleotide (UDP-Gal.2Na) was added to the reaction solution, 500 µl (950 mU) of a different glycosyltransferase (β4GalTI) was added to the reaction solution and a Gal transfer reaction was performed. After 156 hours, when the Gal transfer had progressed 100%, the reaction was stopped by boiling for 5 minutes. After concentrating the reaction solution, the solution was applied to an ODS column chromatography (2.5×50 cm) equilibrated (2.0 ml/min) with 5% MeOH. After eluting a non-absorbed part by 5% MeOH (760 ml), and after fractionating into 20 ml per tube by an MeOH linear concentration gradient method of 5% (500 ml)-15% (500 ml), each fraction was measured by 210 nm absorbance and a product was confirmed. After concentrating a fraction which is number 28-38 (560-760 ml) including the desired product, the product was freeze dried and N-(ε-Trifluororoacetamidocaproyl)-β-lacto-N-neotetraosylamine which is the N-linked asialo-sugar with an extended glycan to a non-reducing terminal was obtained with a weight of 67 mg and yield of 80%.

In process 3, the N-linked asialo-glycan synthesized in process 1-C-1, 1-C-3 and the N-linked asialo-glycan obtained by performing an extension reaction in process 2 are explained below by a process 3-A for deprotecting a protection group, and a process 3-B for condensing the N-linked asialo-glycan performed the deprotection treatment in process 3-A with γ-polyglutamic acid.

(3-A-1) Chemical Synthesis of N-(ε-Aminocaproyl)-β-lactosylamine 1.0M NaOH (1.5 ml) was added to and dissolved in N-(ε-Trifluororoacetamidocaproyl)-β-lactosylamine (150 mg, 0.27 mmol) synthesized in process 1-C-1 and a reaction was started at room temperature. The reaction was confirmed using an orcinol sulfate color reaction and a phosphomolybdic acid color reaction with a TLC (development solution chloroform:methanol:water=6:4:1) every 30 minutes from the start of the reaction. After one hour, the reaction solution confirmed with raw material consumption by TCL was applied to Sephadex G-25 column chromatography (2.5×55 cm) equilibrated (0.5 ml/min) with water. Sampling of a moving layer which passed through a column about every 3.0 ml was performed. The product of the elution fraction was confirmed using a phosphomolybdic acid color reaction with TLC (development solution chloroform:methanol:water=6:4:1). The desired substance was observed at fraction number 47-58 (141 ml-174 ml). This was concentrated and N-(ε-Aminocaproyl)-β-lactosylamine, the desired product of this process, was obtained with a weight of 123 mg and yield of 99%.

(3-A-2) Chemical Synthesis of N-(ε-Aminocaproyl)-β-N-aceyllactosaminylamine 1.0M NaOH (1.6 ml) was added to and dissolved in N-(ε-Trifluororoacetamidocaproyl)-β-N-aceyllactosaminylamine (160 mg, 0.27 mmol) synthesized in process 1-C-3 and a reaction was started at room temperature. The reaction was confirmed using an orcinol sulfate color reaction and a phosphomolybdic acid color reaction with a TLC (development solution chloroform:methanol:water=6:4:1) every 30 minutes from the start of the reaction. After 1 hour, after confirming that the raw material had been consumed by TLC, the reaction solution was applied to a Sephadex G-25 column chromatography (2.5×55 cm) equilibrated (0.5 ml/min) with water. Sampling of a moving layer which passed through a column every 3.0 ml was performed. The product of elution fraction was confirmed using a phosphomolybdic acid color reaction with TLC (development solution chloroform:methanol:water=6:4:1). The desired product was observed with a fraction number of 45-56 (135 ml-168 ml). This was concentrated and N-(ε-Aminocaproyl)-β-N-aceyllactosaminylamine which was the desired product of this process was obtained with a weight of 123 g and yield of 92%.

(3-A-3) Chemical Synthesis of N-(ε-Aminocaproyl)-β-lacto-N-neotetraosylamine 1.0M NaOH (1.0 ml) was added to and dissolved in N-(ε-Trifluororoacetamidocaproyl)-β-lacto-N-neotetraosylamine (45 mg, 0.05 mmol) obtained in process 2 and a reaction was started at room temperature. The reaction was confirmed using an orcinol sulfate color reaction and a phosphomolybdic acid color reaction with a TLC (development solution chloroform:methanol:water=6:4:1) every 30 minutes from the start of the reaction. After 1 hour, after confirming that the raw material had been consumed by TLC, the reaction solution was applied to a Sephadex G-25 column chromatography (2.5×55 cm) equilibrated (0.5 ml/min) with water. Sampling of a moving layer which passed through a column every 3.0 ml was performed. The product of elution fraction was confirmed using a phosphomolybdic acid color reaction with TLC (development solution chloroform:methanol:water=6:4:1). The desired product was observed with a fraction number of 50-61 (150 ml-183 ml). This was concentrated and N-(ε-Aminocaproyl)-β-lacto-N-neotetraosylamine which was the desired product of this process was obtained with a weight of 40 mg and yield of 99%.

(3-B-1) Synthesis of Poly[N-(ε-aminocaproyl)-β-lactosylamine/-γ-PGA]]

After dissolving γ-PGA (M.W.:990000, 30.0 mg) in 100 mM Na$_2$CO$_3$/NaHCO$_3$ pH10.0 (3.6 ml), a condensation agent (BOP:298 mg) dissolved in DMSO (10.9 ml) in advance and an additive (HOBt:29.5 mg) were added and stirred using a stirrer. Lastly, after dissolving and adding N-(ε-Aminocaproyl)-β-lactosylamine (45.1 mg) obtained in process 3-A-1 in 100 mM Na$_2$CO3/NaHCO$_3$ pH10.0 (1.8 ml), a reaction was performed for 24 hours at room temperature while stirring. After the reaction was complete, PBS was added so that the reaction solution became 17.5 ml. Following this, 2.5 ml of the reaction solution for each PD-10 column was applied to a PD-10 (1.7×5.0 cm, Sephadex G-25) column equilibrated with PBS and Poly[N-(ε-aminocaproyl)-β-lactosylamine/-γ-PGA] was eluted by 3.5 ml of PBS. Next, this fraction was dialyzed in 2.5 L of ultra pure water for 3 days. The ultra pure water was exchanged 6 times during this period. After dialysis, concentration and freeze drying was performed. Next, this was applied to a structure analysis by $^1$H-NMR and a sugar exchange rate was calculated. Calculation of the sugar residue exchange rate (%) is as follows. The sum (A) of an integral ratio of β and γ position protons of γ-PGA and 2 protons of an α position of an aglycone portion of N-(ε-aminocaproyl)-β-lactosylamine and an integral ratio (B) of 6 protons of an aglycone portion position of N-(ε-aminocaproyl)-β-lactosylamine was calculated by $^1$H-NMR by inserting into the formula shown below. As a result, N-(ε-aminocaproyl)-β-lactosylamine with a sugar residue exchange rate 31% and a weight of 34.3 mg was obtained.

$$\frac{4 \times 100}{A - 2(B/6)}$$ (Calculation formula)

(3-B-2) Poly[N-(ε-aminocaproyl)-β-N-acetyllactosaminylamine/-γ-PGA]]

After dissolving γ-PGA (M.W.:990000, 30.0 mg) in 100 mM Na$_2$CO$_3$/NaHCO$_3$ pH10.0 (3.6 ml), BOP (298 mg) dissolved in DMSO (10.9 ml) in advance and HOBt (29.5 mg) were added and stirred using a stirrer. Lastly, after dissolving and adding N-(ε-Aminocaproyl)-β-N-acetyllactosaminylamine (49.3 mg) obtained in process 3-A-2 in 100 mM Na$_2$CO$_3$/NaHCO$_3$ pH10.0 (1.8 ml), a reaction was performed for 24 hours at room temperature while stirring. After the reaction was complete, PBS was added so that the reaction solution became 17.5 ml. Following this, 2.5 ml of the reaction solution for each PD-10 column was applied to a PD-10 (1.7×5.0 cm, Sephadex G-25) column equilibrated with PBS and Poly[N-(ε-aminocaproyl)-β-N-acetyllactosaminylamine/-γ-PGA] was eluted by 3.5 ml of PBS. Next, this fraction was dialyzed in 2.5 L of ultra pure water for 3 days. The ultra pure water was exchanged 6 times during this period. After dialysis, concentration and freeze drying was performed. Next, this was used in a structure analysis by $^1$H-NMR and a sugar exchange rate was calculated. Calculation of the sugar residue exchange rate (%) is as follows. A sum (A) of β and γ position protons of γ-PGA and 2 protons of an α position of an aglycone portion of N-(ε-aminocaproyl)-β-N-acetyllactosaminylamine and 3 protons derived from an N-acetyl group, and an integral ratio (B) of 6 protons of an aglycone portion position of N-(ε-aminocaproyl)-β-N-acetyllactosaminylamine was calculated by $^1$H-NMR by inserting into the formula shown below. As a result, N-(ε-aminocaproyl)-β-N-acetyllactosaminylamine with a sugar residue exchange rate 32% and a weight of 36.6 mg was obtained.

$$\frac{4 \times 100}{A - 5(B/6)}$$ (Calculation formula)

(3-B-3) Poly[N-(ε-aminocaproyl)-β-lacto-N-neotetraosylamine/-γ-PGA]]

After dissolving γ-PGA (M.W.:990000, 12.0 mg) in 100 mM Na$_2$CO$_3$/NaHCO$_3$ pH10.0 (1.4 ml), BOP (94.7 mg) dissolved in DMSO (4.4 ml) in advance and HOBt (11.8 mg) were added and stirred using a stirrer. Lastly, after dissolving and adding N-(E-Aminocaproyl)-β-lacto-N-neotetraosylamine (32.6 mg) obtained in process 3-A-3 in 100 mM Na$_2$CO$_3$/NaHCO$_3$ pH10.0 (0.7 ml), a reaction was performed for 24 hours at room temperature while stirring. After the reaction was complete, PBS was added so that the reaction solution became 7.5 ml. Following this, 2.5 ml of the reaction solution for each PD-10 column was applied to a PD-10 (1.7×5.0 cm, Sephadex G-25) column equilibrated with PBS and Poly[N-(ε-aminocaproyl)-β-lacto-N-neotetraosylamine/-γ-PGA] was eluted by 3.5 ml of PBS. Next, this fraction was dialyzed in 2.5 L of ultra pure water for 3 days. The ultra pure water was exchanged 6 times during this period. After dialysis, concentration and freeze drying was performed. Next, this was used in a structure analysis by $^1$H-NMR and a sugar exchange rate was calculated. Calculation of the sugar residue exchange rate (%) is as follows. A sum (A) of β and γ position protons of γ-PGA and 2 protons of an α position of an aglycone portion of N-(ε-aminocaproyl)-β-lacto-N-neotetraosylamine and 3 protons derived from an N-acetyl group, and an integral ratio (B) of 6 protons of an aglycone portion position of N-(ε-aminocaproyl)-β-lacto-N-neotetraosylamine was calculated by $^1$H-NMR by inserting into the formula shown below. As a result, N-(ε-aminocaproyl)-β-lacto-N-neotetraosylamine with a sugar residue exchange rate of 32% and a weight of 19.6 mg was obtained.

$$\frac{4 \times 100}{A - 5(B/6)} \quad \text{(Calculation formula)}$$

Lastly, process 4 in which the three type of asialo-glycan-containing polymers synthesized in process 3 are sialylated and an N-linked sialo-glycan-containing polymer is synthesized is explained. Process 4 was performed according to a known method. Sialic acid was introduced to the asialo-glycan-containing polymer by an enzyme reaction using a CMP sialic acid and glycosyltransferase.

(4-1) Poly[Neu5Ac α2-3lactosylamine β-N-(ε-aminocaproyl)/γ-PGA]

A reaction solution was prepared with 7.1 mg of Poly[N-(ε-aminocaproyl)-β-lactosylamine/γ-PGA] $_{[31\%,\ 1800\ kDa]}$ synthesized in process (3-B-1) as a receptor, 8.0 mM per unit of lactose, CMP sialic acid (CMP-Neu5Ac) 16.0 mM as a donor, MnCl$_2$ 2.5 mM, bovine serum albumin (BSA) 0.1%, and MOPS buffer (pH7.4) 50 mM. Next, 10 U/ml of an alkaline phosphates and 40 mU/ml of a rat α2,3-(N)-sialyltransferase were added, and a reaction was performed for 48 hours at 37° C. Then, this reaction solution was treated by the same method as in process (3-B-1). Calculation of the sialylation rate is as follows. An integral ratio (A) of 1 proton of a 1 position of Glc of N-(ε-aminocaproyl)-β-lactosylamine, and an integral ratio (B, B') of a characteristic 3 position equatorial proton and axial proton of Neu5Ac was calculated by $^1$H-NMR by inserting into the formula shown below. As a result, Poly[Neu5Ac α2,3-lactosylamine β-N-(ε-aminocaproyl)/γ-PGA] with a sialylation rate of 100% and a weight of 8.4 mg was obtained.

$$\frac{(B + B')/2 \times 100}{A/1} \quad \text{(Calculation formula)}$$

(4-2) Poly[Neu5Ac α2-3-N-acetyllactosaminylamine β-N-(ε-aminocaproyl)/γ-PGA]

A reaction solution was prepared with 7.0 mg of Poly[N-(ε-aminocaproyl)-β-N-acetyllactosaminylamine/γ-PGA]$_{[32\%,\ 1900\ kDa]}$ synthesized in process (3-B-2) as a receptor, 8.0 mM per unit of LacNAc, CMP-Neu5Ac 16.0 mM as a donor, MnCl$_2$ 2.5 mM, BSA 0.1%, and MOPS buffer (pH7.4) 50 mM. Next, 10 U/ml of an alkaline phosphates and 40 mU/ml of a rat α2,3-(N)-sialyltransferase were added, and a reaction was performed for 48 hours at 37° C. Then, this reaction solution was treated by the same method as in process (3-B-2). Calculation of the sialylation rate is as follows. An integral ratio (A) of 1 proton of a 1 position of GlcNAc of N-(ε-aminocaproyl)-β-N-acetyllactosaminylamine, and an integral ratio (B) of a characteristic 3 position equatorial proton of Neu5Ac was calculated by $^1$H-NMR by inserting into the formula shown below. As a result, Poly[Neu5Ac α2-3-N-acetyllactosaminylamine β-N-(ε-aminocaproyl)/-γ-PGA] with a sialylation rate of 100% and a weight of 7.9 mg was obtained.

$$\frac{B \times 100}{A/1} \quad \text{(Calculation formula)}$$

(4-3) Poly[Neu5Ac α2-3lacto-N-neotetraosylamine β-N-(ε-aminocaproyl)/γ-PGA]

A reaction solution was prepared with 5.1 mg of Poly[N-(ε-aminocaproyl)-β-lacto-N-neotetraosylamine/γ-PGA]$_{[32\%,\ 2600\ kDa]}$ synthesized in process (3-B-3) as a receptor, 8.0 mM per unit of LNnT, CMP-Neu5Ac 16.0 mM as a donor, MnCl$_2$ 2.5 mM, BSA 0.1%, and MOPS buffer (pH7.4) 50 mM. Next, 10 U/ml of an alkaline phosphates and 40 mU/ml of a α2,3-(N)-sialyltransferase were added, and a reaction was performed for 48 hours at 37° C. Then, this reaction solution was treated by the same method as in process (3-B-3). Calculation of the sialylation rate is as follows. An integral ratio (A) of 1 proton of a 1 position of Glc of N-(ε-aminocaproyl)-β-lacto-N-neotetraosylamine, and an integral ratio (B, B') of a characteristic 3 position equatorial proton and axial proton of Neu5Ac was calculated by $^1$H-NMR by inserting into the formula shown below. As a result, Poly[Neu5Ac α2-3lacto-N-neotetraosylamine β-N-(ε-aminocaproyl)/γ-PGA] with a sialylation rate of 100% and a weight of 5.2 mg was obtained.

$$\frac{(B+B')/2\times 100}{A/1}$$ (Calculation formula)

(4-4) Poly[Neu5Ac α2-6lactosylamine β-N-(ε-aminocaproyl)/γ-PGA]

Instead of the enzyme, the same process as process 4-1 was performed. Specifically, a reaction solution was prepared with 7.0 mg of Poly[N-(ε-aminocaproyl)-β-lactosylamine/γ-PGA]$_{[31\%, 1800\, kDa]}$ synthesized in process (3-B-1) as a receptor, 8.0 mM per unit of Lactose, CMP-Neu5Ac 16.0 mM as a donor, MnCl$_2$ 2.5 mM, BSA 0.1%, and MOPS buffer (pH7.4) 50 mM. Next, 10 U/ml of an alkaline phosphates and 40mU/ml of a α2,6-(N)-sialyltransferase were added, and a reaction was performed for 48 hours at 37° C. Then, this reaction solution was treated by the same method as in process (3-B-1). Calculation of the sialylation rate is as follows. An integral ratio (A) of 1 proton of 1 position of Glc of N-(ε-aminocaproyl)-β-lactosylamine, and an integral ratio (B, B') of a characteristic 3 position equatorial proton and axial proton of Neu5Ac was calculated by $^1$H-NMR by inserting into the formula shown below. As a result, Poly[Neu5Ac α2-6lactosylamine β-N-(ε-aminocaproyl)/γ-PGA] with a sialylation rate of 71% and a weight of 7.2 mg was obtained.

$$\frac{(B+B')/2\times 100}{A/1}$$ (Calculation formula)

(4-5) Poly[Neu5Ac α2-6-N-acetyllactosaminylamine β-N-(ε-aminocaproyl)/γ-PGA]

Instead of the enzyme, the same process as process 4-2 was performed. Specifically, a reaction solution was prepared with 7.0 mg of Poly[N-(ε-aminocaproyl)-β-N-acetyllactosaminylamine/γ-PGA]$_{[32\%, 1900\, kDa]}$ synthesized in process (3-B-2) as a receptor, 8.0 mM per unit of LacNAc, CMP-Neu5Ac 16.0 mM as a donor, MnCl$_2$ 2.5 mM, BSA 0.1%, and MOPS buffer (pH7.4) 50 mM. Next, 10 U/ml of an alkaline phosphates and 40 mU/ml of a rat α2,6-(N)-sialyltransferase were added, and a reaction was performed for 48 hours at 37° C. Then, this reaction solution was treated by the same method as in process (3-B-2). Calculation of the sialylation rate is as follows. An integral ratio (A) of 1 proton of 1 position of GlcNAc of N-(ε-aminocaproyl)-β-lactosylamine, and an integral ratio (B, B') of a characteristic 3 position equatorial proton and axial proton of Neu5Ac was calculated by $^1$H-NMR by inserting into the formula shown below. As a result, Poly[Neu5Ac α2-6-N-acetyllactosaminylamine β-N-(ε-aminocaproyl)/γ-PGA] with a sialylation rate of 100% and a weight of 7.9 mg was obtained.

$$\frac{(B+B')/2\times 100}{A/1}$$ (Calculation formula)

(4-6) Poly[Neu5Ac α2-6-lacto-N-neotetraosylamine β-N-(ε-aminocaproyl)/γ-PGA]

Instead of the enzyme, the same process as process 4-3 was performed. Specifically, a reaction solution was prepared with 5.1 mg of Poly[N-(ε-aminocaproyl)-β-lacto-N-neotetraosylamine/γ-PGA]$_{[32\%, 2600\, kDa]}$ synthesized in process (3-B-3) as a receptor, 8.0 mM per unit of LNnT, CMP-Neu5Ac 16.0 mM as a donor, MnCl$_2$ 2.5 mM, BSA 0.1%, and MOPS buffer (pH7.4) 50 mM. Next, 10 U/ml of an alkaline phosphates and 40mU/ml of a α2,6-(N)-sialyltransferase were added, and a reaction was performed for 48 hours at 37° C. Then, this reaction solution was treated by the same method as in process (3-B-3). Calculation of the sialylation rate is as follows. An integral ratio (A) of 1 proton of 1 position of Glc of N-(ε-aminocaproyl)-β-lacto-N-neotetraosylamine, and an integral ratio (B, B') of a characteristic 3 position equatorial proton and axial proton of Neu5Ac was calculated by $^1$H-NMR by inserting into the formula shown below. As a result, Poly[Neu5Ac α2-6-lacto-N-neotetraosylamine β-N-(ε-aminocaproyl)/γ-PGA] with a sialylation rate of 100% and a weight of 5.4 mg was obtained.

$$\frac{(B+B')/2\times 100}{A/1}$$ (Calculation formula)

Example 2

Synthesis of Synthetic sialo-glycan-containing Polymer by Production Method 2

(1) Synthesis of N-(ε-Trifluoroacetamidocaproyl)-β-N-acetylglucosaminylamine In process 1 of example 2, a linker chemical compound with a protected amino group was condensed with a 1-amino sugar and N-(ε-Trifluoroacetamidocaproyl)-β-N-acetylglucosaminylamine (GlcNAc-6AHA-TFA) was prepared by the same method described in process (1-C-3) in example 1.

(2) Synthesis of N-(ε-aminocaproyl)-β-neu5Ac-α2, 6-N-acetyllactosaminylamine (α2,6-SLN-6AHA)

In process 2, after the N-linked asialo-glycan (GlcNAc-6AHA-TFA) prepared in process 1 was sialylated and a sialoglycan part was synthesized (process 2-1), this was purified (process 2-2). This is explained in detail below.

(2-1) Synthesis of sialo-glycan Part

*H. Influenzae* derived β1,4-galacutosetransferase was added to a 100 mM Tris-HCl buffer (pH7.5) 190 ml containing 420 mg (1.04 mmol) GlcNAc-6AHA-TFA prepared in process (1), 20 mM magnesium chloride, 7.5M UDP-Gal, 0.1 U/ml of alkaline phosphates solution, so that a reaction solution became 0.16 U/ml of β1,4-galacutosyltransferase and a reaction was started while shaking at 37° C. After 26 hours had passed since the start of the reaction, the reaction solution was transferred to a boiling bath and the β1,4-galacutosyltransferase reaction was stopped by increasing the temperature of the solution to 80° C. After sufficiently cooling the β1,4-galacutosyltransferase which has been heat treated, 7.5 mM CMP-NeuAc, 50 mM Tris-HCl buffer (pH7.5) was again added, a *p. damselae* derived α2,6-sialyltransferase was added so that the reaction solution becomes 0.1 U/ml α2,6-sialyltransferase and a sialylation was started while shaking at 37° C. After 17 hours had passed since the start of the reaction, the solution was transferred to the boiling bath and the α2,6-sialyltransferase reaction was stopped by increasing the temperature of the solution to 80° C., and an N-linked sialo-glycan (α2,6-SLN-6AHA-TFA) having a sialo-glycan part on a non-reducing terminal was synthesized.

(2-2) Purification of N-linked sialo-glycan

The N-linked sialo-glycan synthesized by the sequence described above was purified by the sequence described below. First, after cooling the reaction stopped solution of process (2-1), centrifugal separation (20,000×g 10 min) was performed and by filtrating the supernatant obtained by a 0.45 μm filter, a residue was completely removed and a supernatant fraction was collected. This was passed through an ODS column (200 ml) equilibrated with 50 mM ammonium hydrogen carbonate, and after adsorbing α2,6-SLN-6AHA-TFA, hydrophilic substances such as nucleic acids or sugars were removed by washing with 50 mM ammonium hydrogen carbonate. After eluting α2,6-SLN-6AHA-TFA which was absorbed into an absorbent by ammonium hydrogen carbonate including 10% methanol, and the contained ammonium hydrogen carbonate was removed by concentrating and drying by an evaporator, and azeotroping with water. After dissolving the α2,6-SLN-6AHA-TFA dried substance prepared by the above sequence to 50 ml by distilled water, the α2,6-SLN-6AHA-TFA was absorbed into a column by passing through a DEAE column (50 ml, hydrogen carbonate). After removing any remaining asialo-glycan by washing this column with distilled water, α2,6-SLN-6AHA-TFA which was absorbed into the column by passing through 50 mM ammonium hydrogen carbonate, is eluted.

(3-1) Deprotection of a Protection Group

Because α2,6-SLN-6AHA-TFA has a protection group (TFA group) which protects an amino acid, the protection group is deprotected before a condensation reaction was performed with polyglutamic acid. Specifically, after drying by concentrating α2,6-SLN-6AHA-TFA obtained by the above described process under a reduced pressure, by dissolving in 1M NaOH and stirring for 1 hour at room temperature, the TFA within α2,6-SLN-6AHA-TFA was deprotected.

After neutralizing the deprotected TFA solution by 0.5M hydrochloride, the solution was passed through a Sephadex G-25 column (1.6×100 cm) equilibrated with 50 mM ammonium hydrogen carbonate. The fractionated fraction including sugar was spotted on TLC, confirmed by anisaldehyde color reaction and the fraction containing the obtained sugar was collected. After concentrating this under reduced pressure, drying and azeotroping with methanol, by reduced pressure drying for 2 hours at 50° C., 357 mg (0.48 mmol) of ammonium salt of the N-linked sialo-glycan (α2,6-SLN-6AHA) with released protection group was collected.

(3-2) Synthesis of Poly[Neu5Ac α2,6-N-acetyllactosaminylamine β-N-(ε-aminocarproyl)/γ-PGA] (α2,6-SLN-6AHA/γ-PGA)

Next, ammonium salt of (α2,6-SLN-6AHA) obtained in process 3-1 and γ-polyglutamic acid were condensed. Specifically, distilled water 0.05 ml, DMF 0.45 ml were added to γ-PGA (4.3 mg, 0.033 mmol as Glu), turned into a uniform solution and cooled to 0° C. in an ice bath. HOSu (1.4 mg, 0.012 mmol), EDC (2.6 mg, 0.013 mmol) was added to the γ-PGA solution as a condensing agent and stirred for 2 hours at 0° C. Then, α2,6-SLN-6AHA (11.2 mg, 0.013 mmol), Triethylamine (13.8 uL, 0.1 mmol) was added to the reaction solution, stirred for hours at 25° C., and Poly[Neu5Ac α2,6-N-acetyllactosaminylamine β-N-(ε-aminocarproyl)/γ-PGA] (α2,6-SLN-6AHA/γ-PGA) was synthesized. After the reaction solution was cooled to 0° C., 1.0M NaOH water solution 0.5 ml was added, stirred for 30 minutes at 0° C. and the reaction was stopped.

(4) Isolation of Poly[Neu5Ac α2,6-N-acetyllactosaminylamine β-N-(ε-aminocarproyl)/γ-PGA] (α2,6-SLN-6AHA/γ-PGA)

The above described reaction solution was adjusted to pH7 using 1.0M AcOH water solution, this was inserted into a dialysis tube and dialysis was performed in distilled water (1000 ml ×7). The solution within the dialysis tube was collected, passed though an ion exchange column (Dowex AG 50W-8X, Na form, CV=2 ml), and converted to Na salt. The collected solution was concentrated under reduced pressure, any residue was dissolved in a small amount of distilled water, and by freeze drying, 12.2 mg of α2,6-SLN-6AHA/γ-PGA white powder was obtained. $^1$H-NMR analysis was performed on the obtained α2,6-SLN-6AHA/γ-PGA and as a result of measuring the sugar residue exchange rate (DS) based on the formula below, 37% was eluted.

$DS=A/(B-A/2-3A/4-3C\times 3A/4)$

A=1.5 ppm: 6AHA (2CH$_2$)
B=1.8-2.5 ppm: (γ-PGA(2CH$_2$)+Ac(GlcNAc)+Ac(NeuAc)+ 6AHA(CH$_2$)
C=2.7 ppm: NeuAc(2-CH')

Example 3

Hemagglutination Inhibition Assay of a Polypeptide Containing Various Synthetic Glycans Using Influenza A Virus A microplate used for hemagglutination activity assay was placed on ice and 25 ul of PBS containing 0.01% gelatine was added to each well. Next, 3 types of polypeptide containing synthetic asialo-glycans prepared in process 3-B of example 1 and 6 types of polymer containing synthetic sialo-glycans prepared in process 4 were dissolved in PBS containing 0.01% gelatine, each 25 ul was added to No. 1 well, and prepared so that each was continuously diluted twice from well No. 2. Then, each well which has the diluted sample was added with 25 ul each of an influenza virus (Human strain: A/Aichi/2/28 (H3N2) suspended by PBS, infectivity titer $2^{20}$ HAU, Avian strain:A/Duck/HongKong/313/4/76 (H5N2), and infectivity titer $2^{17}$ HAU) (each $2^2$ HAU), and after stirring for a few seconds with a microplate mixer, was left for 1 hour at 4° C. 50 ul of a PBS suspended solution containing 0.6% (v/v) guinea pig red blood cells was added to each well and was left for 2 hours at 4° C. after stirring for a few seconds with a microplate mixer. Lastly, a hemagglutination was observed and HI activity (Hemagglutination inhibition activity) was measured. The HI activity was expressed by the maximum diluted concentration of a sample in which complete agglutination inhibition of the influenza virus was acknowledged.
[Table 1]

TABLE 1

Hemagglutination inhibition assay of a synthetic sialo-glycan polymer using an influenza virus.

| glycopolypeptides | HI activity IC$_{50}$ (nM) | |
| --- | --- | --- |
| | A/Aichi/2/68 (H3N2) | A/Duck/HK/313/4/78 (H5N3) |
| γ-PGA$^a$ | >200 | >200 |
| Poly[N-(ε-aminocaproyl)-β-lactosylamine/γ-PGA] | >200 | >200 |
| Poly[N-(ε-aminocaproyl)-β-acetyllactosaminylamine/γ-PGA] | >200 | >200 |
| Poly[N-(ε-aminocaproyl)-β-lacto-N-neotetraosylamine/γ-PGA] | >200 | >200 |
| Poly (Neu5Acα2-3lactosylamine β-N-(ε-aminocaproyl)/γ-PGA) | 37.5 | 37.5 |
| Poly (Neu5Acα2-3-N-acetyllactosaminylamine β-N-(ε-aminocaproyl)/γ-PGA) | 37.5 | 37.5 |
| Poly (Neu5Acα2-3-lacto-N-neotetraosylamine β-N-(ε-aminocaproyl)/γ-PGA) | 18.8 | 37.5 |
| Poly (Neu5Acα2-6lactosylamine β-N-(ε-aminocaproyl)/γ-PGA) | 4.7 | >200 |
| Poly (Neu5Acα2-6-N-acetyllactosaminylamine β-N-(ε-aminocaproyl)/γ-PGA) | 1.2 | >200 |
| Poly (Neu5Acα2-6-lacto-N-neotetraosylamine β-N-(ε-aminocaproyl)/γ-PGA) | 0.29 | >200 |

As is clear from Table 1, the N-linked Poly(Neu5Ac α2-6-LacNAc β-N-(ε-aminocarproyl)/γ-PGA) (chemical compound second from bottom in Table 1) prepared in example 1, shows an inhibition activity of human influenza virus infection many times greater than an O-linked synthetic sialo-glycan-containing polymer (Poly(Neu5Ac α2-6-LacNAc β-5-aminopentyl/γ-PGA) which has the same structure as a conventional glycan part reported in document (Bioog. Med. Chem., 15, 1383-1393 (2007)), and in addition, Poly [Neu5Ac α2-6lacto-N-neotetraosylamine β-N-(ε-aminocarproyl)/γ-PGA] (chemical compound at the bottom of Table 1) showed an inhibition activity of human influenza virus infection many more times greater than Poly[Neu5Ac α2-6-LacNAc β-N-(ε-aminocarproyl/γ-PGA].

The present invention provides a sialo-glycan-containing polymer which shows an inhibition activity of influenza virus infection many times greater than a conventional sialo-glycan-containing polymer and can change the binding form between the sialo-glycan part of a conventional sialo-glycan-containing polymer and a linker, and can be produced at a low cost and good yield. More specifically with respect to the yield, when synthesizing a conventional O-linked sialo-glycan-containing polymer, a *trichoderma* derived cellulase purified to a high level is required in the condensation of the asialo-glycan part and aminoalkyl alcohol which becomes the linker, and a chemical compound could only be synthesized with an extremely low synthesis yield (about 1% of the glycan used). Whereas, simply by changing to an N-linked type it is possible to synthesize a desired chemical compound with a synthesis yield of 80% or more.

This type of sialo-glycan-containing polymer of the present invention can be applied to various means for preventing influenza virus infection or the spread of influenza. Removing an influenza virus from the air by filling in a filter or prevention of proliferation or prevention of infection of a virus by filling up a mask as a virus absorbent is very useful. Furthermore, if the sialic acid applied to the non-reducing terminal of the glycan part is a α2,3 type, the invention can also be used as an infection inhibition agent against the avian influenza virus.

Furthermore, a condensation reaction between the sialo-sugar part and polyglutamic acid was a very difficult reaction. However, according to the production method of the present invention, the solubility of the polyglutamic acid can be improved by using a contained water based mixed solvent which is different from convention, active esterification of the carboxyl group within the polyglutamic acid can be performed uniformly even without using an excessive amount of reagent and because an excessive reagent does not exist in the polyglutamic solution which is active esterified in this way, it is possible to prevent a condensation reaction between sialo-glycans due to an excessive amount of reagent seen in the conventional method, and because it is possible to improve the efficiency of the condensation of the sialo-glycan part and polyglutamic acid via a linker without protecting a carboxyl group of the sialo-glycan, for the first time it is possible to provide a practical production method of a sialo-glycan-containing polymer.

What is claimed is:

1. A production method of an N-linked sialo-glycan-containing polymer comprising:
   forming an amide bond between (i) a linker compound having an amino group and a carboxyl group on each end of the compound respectively and (ii) a 1-amino sugar in which a 1 position of a reducing terminal of the sugar is aminated, thereby obtaining an N-linked asialo-glycan having an asialo-glycan part on a non-reducing terminal of a sugar;
   obtaining an N-linked sialo-glycan in which a sialo-glycan is synthesized to the non-reducing terminal side by sialylation of the N-linked asialo-glycan; and
   synthesizing a sialo-glycan-containing polymer by condensing the N-linked sialo-glycan to a carboxyl group of a γ-polyglutamic acid via the amino group of the linker, which is linked to a reducing terminal of the N-linked sialo-glycan, wherein the linker is an w-amino acid comprising a hydrocarbon with a carbon number of 1-30 that is an alkyl group, an alkenyl group, a cycloalkyl group, an aryl group, an aralkyl group, a cycloalkyl substituted alkyl group or an amide linked hydrocarbon of two or more of these, and wherein the γ-polyglutamic acid is dissolved in a mixed solution comprising (i) water or a buffer and (ii) an organic solvent, and the N-linked sialo-glycan is condensed with the γ-polyglutamic acid after activating the γ-polyglutamic acid using an active esterification agent of a carboxyl group, condensing agent, and/or additive.

* * * * *